(12) United States Patent
Peichel et al.

(10) Patent No.: US 11,213,684 B2
(45) Date of Patent: Jan. 4, 2022

(54) DEVICE AND METHOD TO REDUCE ARTIFACT FROM TISSUE CONDUCTION COMMUNICATION TRANSMISSION

(71) Applicant: Medtronic, Inc., Minneapolis, MN (US)

(72) Inventors: David J. Peichel, Minneapolis, MN (US); James D. Reinke, Maple Grove, MN (US); Jonathan P. Roberts, Coon Rapids, MN (US); Michael B. Terry, Camas, WA (US)

(73) Assignee: Medtronic, Inc., Minneapolis, MN (US)

( * ) Notice: Subject to any disclaimer, the term of this patent is extended or adjusted under 35 U.S.C. 154(b) by 113 days.

(21) Appl. No.: 16/203,939

(22) Filed: Nov. 29, 2018

(65) Prior Publication Data
US 2019/0160291 A1    May 30, 2019

Related U.S. Application Data

(60) Provisional application No. 62/591,806, filed on Nov. 29, 2017.

(51) Int. Cl.
*A61N 1/372* (2006.01)
*A61N 1/375* (2006.01)
(Continued)

(52) U.S. Cl.
CPC ........ *A61N 1/37217* (2013.01); *A61B 5/0028* (2013.01); *A61B 5/0031* (2013.01);
(Continued)

(58) Field of Classification Search
CPC ............ A61N 1/37217; A61N 1/37288; A61N 1/3756; A61N 1/3956; A61N 1/3962; A61N 1/3975; A61N 1/05; A61N 1/37264; A61N 1/372; A61B 5/0028; A61B 5/0031; A61B 5/686; H04B 13/005
See application file for complete search history.

(56) References Cited

U.S. PATENT DOCUMENTS

| 4,987,897 A | 1/1991 | Funke |
| 5,591,214 A | 1/1997 | Lu |

(Continued)

FOREIGN PATENT DOCUMENTS

| WO | 2016118845 A1 | 7/2016 |
| WO | 2016118847 A1 | 7/2016 |

OTHER PUBLICATIONS

Zhao et al., "Device, System and Method With Adaptive Timing for Tissue Conduction Communication Transmission ", U.S. Appl. No. 16/220,093, filed Dec. 14, 2018, 65 pages.
(Continued)

*Primary Examiner* — Christopher A Flory

(57) ABSTRACT

A device is configured to transmit tissue conductance communication (TCC) signals by generating multiple TCC signals by a TCC transmitter of the IMD. The generated TCC signals are coupled to a transmitting electrode vector via a coupling capacitor to transmit the plurality of TCC signals to a receiving medical device via a conductive tissue pathway. A voltage holding circuit holds the coupling capacitor at a DC voltage for a time interval between two consecutively transmitted TCC signals.

24 Claims, 12 Drawing Sheets

(51) Int. Cl.
*A61N 1/39* (2006.01)
*H04B 13/00* (2006.01)
*A61B 5/00* (2006.01)
*A61N 1/05* (2006.01)

(52) U.S. Cl.
CPC ............ *A61B 5/686* (2013.01); *A61N 1/3756* (2013.01); *A61N 1/37288* (2013.01); *A61N 1/3956* (2013.01); *A61N 1/3962* (2013.01); *A61N 1/3975* (2013.01); *H04B 13/005* (2013.01); *A61N 1/05* (2013.01); *A61N 1/37264* (2013.01)

(56) References Cited

U.S. PATENT DOCUMENTS

| | | | |
|---|---|---|---|
| 6,076,016 A | 6/2000 | Feierbach | |
| 6,115,636 A | 9/2000 | Ryan | |
| 7,542,800 B2 | 6/2009 | Libbus et al. | |
| 7,623,930 B2 | 11/2009 | Zeijlemaker et al. | |
| 7,912,537 B2 | 3/2011 | Lee et al. | |
| 8,041,418 B2 | 10/2011 | Giftakis et al. | |
| 8,055,345 B2 | 11/2011 | Li et al. | |
| 8,275,444 B2 | 9/2012 | Zeijlemaker et al. | |
| 8,412,352 B2 | 4/2013 | Griswold et al. | |
| 8,457,742 B2 | 6/2013 | Jacobson | |
| 8,720,726 B2 | 5/2014 | Salinas | |
| 8,738,126 B2 | 5/2014 | Craig | |
| 8,744,572 B1 | 6/2014 | Greenhut et al. | |
| 8,924,008 B2 | 12/2014 | Yuyama et al. | |
| 8,954,008 B2 | 2/2015 | Wang et al. | |
| 8,996,115 B2 | 3/2015 | Trier et al. | |
| 9,168,383 B2 | 10/2015 | Jacobson et al. | |
| 9,636,511 B2 | 5/2017 | Carney et al. | |
| 9,687,659 B2 | 6/2017 | Von Arx et al. | |
| 9,713,434 B2 | 7/2017 | Barak | |
| 2004/0011366 A1 | 1/2004 | Schulman et al. | |
| 2012/0109236 A1* | 5/2012 | Jacobson | A61N 1/37217 607/4 |
| 2012/0109258 A1 | 5/2012 | Cinbis et al. | |
| 2012/0277600 A1 | 11/2012 | Greenhut | |
| 2012/0323099 A1 | 12/2012 | Mothilal et al. | |
| 2013/0253345 A1 | 9/2013 | Griswold et al. | |
| 2013/0324825 A1 | 12/2013 | Ostroff et al. | |
| 2014/0180351 A1* | 6/2014 | Gilman | A61N 1/36542 607/4 |
| 2014/0222109 A1* | 8/2014 | Moulder | A61N 1/37217 607/60 |
| 2014/0277286 A1 | 9/2014 | Cinbis | |
| 2014/0379048 A1* | 12/2014 | Von Arx | A61N 1/362 607/60 |
| 2015/0057721 A1 | 2/2015 | Stahmann et al. | |
| 2015/0306375 A1 | 10/2015 | Marshall et al. | |
| 2015/0306410 A1 | 10/2015 | Marshall et al. | |
| 2016/0144190 A1* | 5/2016 | Cao | A61N 1/36585 607/17 |
| 2016/0213937 A1 | 7/2016 | Reinke et al. | |
| 2016/0213939 A1* | 7/2016 | Carney | A61N 1/3975 |
| 2016/0296760 A1 | 10/2016 | Sahabi et al. | |
| 2017/0157399 A1* | 6/2017 | Anderson | A61N 1/3622 |
| 2017/0173346 A1 | 6/2017 | Kane et al. | |

OTHER PUBLICATIONS (PCT/US2018/062977) PCT Notification of Transmittal of the International Search Report and the Written Opinion of the International Searching Authority, dated Feb. 15, 2019, 11 pages.

Roberts et al., "Signal Transmission Optimization for Tissue Conduction Communication", U.S. Appl. No. 16/202,418, filed Nov. 28, 2018, 32 pages.

Peichel et al., "Tissue Conduction Communication in an Implantable Medical Device System", U.S. Appl. No. 62/591,813, filed Nov. 29, 2017, 93 pages.

Reinke et al., "Tissue Conduction Communication for Implantable Medical Devices", U.S. Appl. No. 62/591,810, filed Nov. 29, 2017, 87 pages.

European Communication Pursuant to Article 94(3) EPC, dated Sep. 16, 2021, European Patent Application 18825834.7, 4 pages.

* cited by examiner

DEVICE AND METHOD TO REDUCE ARTIFACT FROM TISSUE CONDUCTION COMMUNICATION TRANSMISSION

TECHNICAL FIELD

The disclosure relates generally to devices, systems and methods for communicating using tissue conduction communication.

BACKGROUND

Communication between two or more devices associated with a person, e.g., implanted within the person and/or attached to or otherwise contacting the person, may be desirable in a number of applications, such as for monitoring or managing health of a patient. Communication between these devices may, for example, enable the exchange of information, coordinated monitoring of a health condition and/or coordinated therapy to treat health conditions. Such systems, some examples of which are described below, may communicate using tissue conduction communication (TCC). TCC uses the human body as the medium of communication. TCC may sometimes be referred to as human body conduction (HBC) or intrabody communication.

A wide variety of implantable medical devices (IMDs) for delivering a therapy to or monitoring a physiological condition of a patient have been used clinically or proposed for clinical use in patients. Examples include IMDs that deliver therapy to and/or monitor conditions associated with the heart, muscle, nerve, brain, stomach or other tissue. Some therapies include the delivery of electrical stimulation to such tissues. Some IMDs may employ electrodes for the delivery of therapeutic electrical signals to such organs or tissues, electrodes for sensing intrinsic physiological electrical signals within the patient, which may be propagated by such organs or tissue, and/or other sensors for sensing physiological signals of a patient.

Implantable cardioverter defibrillators (ICDs), for example, may be used to deliver high energy defibrillation and/or cardioversion shocks to a patient's heart when atrial or ventricular tachyarrhythmia, e.g., tachycardia or fibrillation, is detected. An ICD may detect a tachyarrhythmia based on an analysis of a cardiac electrogram sensed via electrodes, and may deliver anti-tachyarrhythmia shocks, e.g., defibrillation shocks and/or cardioversion shocks, via electrodes. An ICD or an implantable cardiac pacemaker, as another example, may provide cardiac pacing therapy to the heart when the natural pacemaker and/or conduction system of the heart fails to provide synchronized atrial and ventricular contractions at rates and intervals sufficient to sustain healthy patient function. ICDs and cardiac pacemakers may also provide overdrive cardiac pacing, referred to as anti-tachycardia pacing (ATP), to suppress or convert detected tachyarrhythmias in an effort to avoid cardioversion/defibrillation shocks.

Some IMDs are coupled to one or more of the electrodes used to sense electrical physiological signals and deliver electrical stimulation via one or more leads. A medical electrical lead carrying sensing and/or electrical therapy delivery electrodes allow the IMD housing to be positioned a location spaced apart from the target site for sensing and/or stimulation delivery. For example, a subcutaneously or sub-muscularly implanted housing of an ICD or implantable cardiac pacemaker may be coupled to endocardial electrodes via one or more medical electrical leads that extend transvenously to the patient's heart. Other ICD systems, referred to as extracardiovascular ICD systems, are not coupled to any transvenous leads, and instead sense and deliver shocks via electrodes implanted away from the patient's heart, e.g., implanted subcutaneously or substernally. The extra-cardiovascular electrodes may be provided along the housing of the subcutaneous ICD and/or coupled to the housing via one or more leads extending subcutaneously, submuscularly or substernally from the housing.

Leadless IMDs may also be used to deliver therapy to a patient, and/or sense physiological parameters of a patient. In some examples, a leadless IMD may include one or more electrodes on its outer housing to deliver therapeutic electrical stimulation to patient, and/or sense intrinsic electrical signals of patient. For example, a leadless pacemaker may be used to sense intrinsic depolarizations or other physiological parameters of the patient, and/or deliver therapeutic electrical stimulation to the heart. A leadless pacemaker may be positioned within or outside of the heart and, in some examples, may be anchored to a wall of the heart via a fixation mechanism.

In some situations, two or more IMDs are implanted within a single patient. It may be desirable for the two or more IMDs to be able to communicate with each other, e.g., to coordinate, or cooperatively provide, sensing for monitoring the patient and/or therapy delivery. Although some IMDs communicate with other medical devices, e.g., with external programming devices, using radio-frequency (RF) telemetry TCC allows for communication between two or more IMDs by transmitting signals between the electrodes of two IMDs via a conductive tissue pathway. Likewise, TCC may be utilized to communicate between an IMD and an external device having electrodes proximate to or in contact with the skin of the patient or between two external devices having electrodes proximate to or in contact with the skin of the patient.

SUMMARY

The techniques of this disclosure generally relate to TCC signal transmission techniques performed by a device. The techniques of this disclosure are described in the context of an IMD. However, the techniques can be utilized by any device, medical or non-medical, implanted or external, that communicates using TCC. A TCC transmitter may be included in an IMD configured to communicate with one or more other IMDs co-implanted in a patient and/or an external device coupled to the patient. The TCC transmitter includes a voltage holding circuit for holding a voltage established on an alternating current (AC) coupling capacitor between TCC signal transmissions. The AC coupling capacitor is used to couple TCC signals generated by the TCC transmitter to a transmitting electrode vector for conduction along a conductive tissue pathway to a receiving electrode vector of a receiving device. The voltage holding circuit is used to avoid frequent recharging of the AC coupling capacitor to an operating DC voltage between TCC signal transmissions to eliminate or minimize the likelihood of TCC signal interference with sensing circuitry of the transmitting device and/or other medical devices implanted in or coupled to the patient.

In one example, the disclosure provides a housing and a tissue conduction communication (TCC) transmitter enclosed by the housing. The TCC transmitter is configured to generate a plurality of TCC signals. The TCC transmitter includes a coupling capacitor for coupling the generated TCC signals to a transmitting electrode vector to transmit the plurality of TCC signals via a conductive tissue pathway and a voltage holding circuit configured to hold the coupling capacitor at a direct current (DC) voltage for a time interval between two consecutively transmitted TCC signals of the plurality of TCC signals.

In another example, the disclosure provides a method comprising generating a plurality of tissue conduction communication (TCC) signals, coupling the plurality of generated TCC signals to a transmitting electrode vector via a coupling capacitor to transmit the plurality of TCC signals via a conductive tissue pathway, and holding the coupling capacitor at a direct current (DC) voltage for a time interval between two consecutively transmitted TCC signals of the plurality of TCC signals.

In another example, the disclosure provides a non-transitory, computer-readable storage medium comprising a set of instructions which, when executed by a device cause the device to generate a plurality of tissue conduction communication (TCC) signals, couple the generated TCC signals to a transmitting electrode vector to transmit the plurality of TCC signals via a conductive tissue pathway, and hold the coupling capacitor at a direct current (DC) voltage for a time interval between two consecutively transmitted TCC signals of the plurality of TCC signals.

control circuit of an IMD configured to transmit a TCC signal, cause the IMD to generate TCC signals, couple the generated TCC signals to a transmitting electrode vector coupled to the IMD via a coupling capacitor to transmit the TCC signals to a receiving medical device via a conductive tissue pathway, and hold the coupling capacitor at a DC voltage by a voltage holding circuit for a time interval between two consecutively transmitted TCC signals of the plurality of TCC signals.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Wireless communication between two or more medical devices may be desired for a number of reasons, including to exchange data and/or to coordinate, or cooperatively provide, sensing of physiological signals and/or therapy delivery. TCC signals may be wirelessly transmitted from one IMD to one or more IMDs co-implanted within a patient and/or to an external medical device having skin or surface electrodes coupled to the patient for transmitting and/or receiving TCC signals. Some IMDs and external medical devices may be configured to sense an electrophysiological signal via sensing electrodes and/or monitor electrical impedance such as transthoracic impedance signals. Examples of electrophysiological signals include a cardiac electrical signal produced by the patient's heart, an electromyogram signal produced by skeletal muscle tissue, and other electrophysiological signals produced by the brain, nerve or muscle tissue. Transmission of a communication signal may cause interference with electrical signal sensing circuitry. Transmission of a communication signal through body tissue may unintentionally cause electrical stimulation of muscle or nerves depending on the amplitude and frequency of the transmitted signal.

An IMD or an external medical device that includes electrical signal sensing circuitry configured to receive an electrophysiological signal or monitor impedance may be a TCC transmitting device, an intended TCC receiving device, or an unintended receiving device that is coupled to electrodes within the tissue conduction pathway of a TCC signal being transmitted between two other devices. In each case, a transmitted TCC signal may be received by sensing electrodes coupled to the transmitting or receiving IMD or external device and interfere with the sensing circuitry. In other examples, a transmitting or receiving device may be configured to monitor the electrical impedance of one or more medical electrical leads or the tissue impedance between one or more electrode vectors coupled to the device. A TCC transmitter and transmission techniques are disclosed herein for minimizing the likelihood of a TCC signal interfering with electrophysiological signal sensing circuitry, impedance monitoring, or other monitoring of electrical signals performed by a system.

Figure 1:
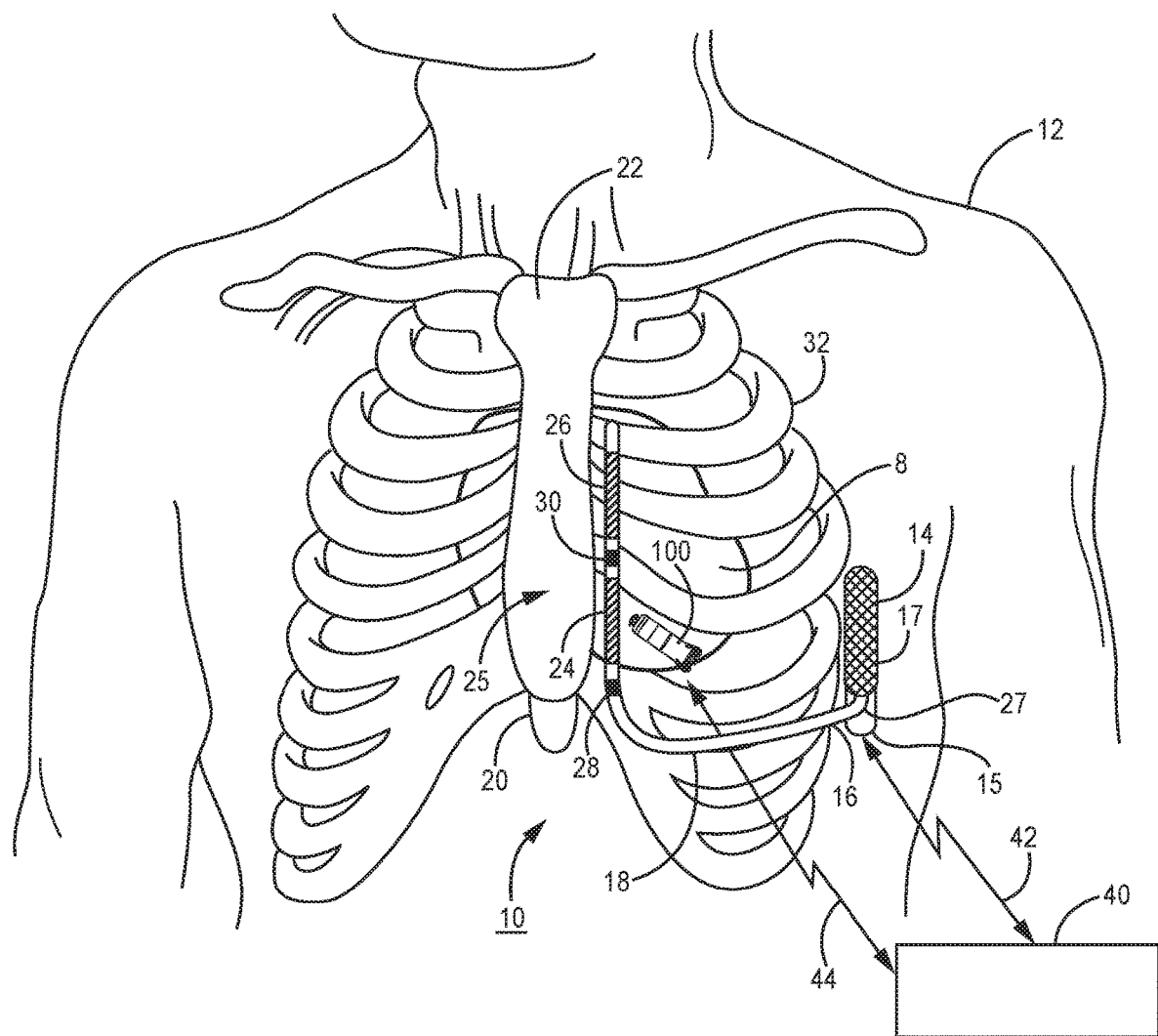
FIG. 1 is a conceptual diagram of an IMD system capable of TCC according to one example.

FIG. 1 is a conceptual diagram of an IMD system 10 capable of TCC according to one example. FIG. 1 is a front view of a patient 12 implanted with IMD system 10. IMD system 10 includes an ICD 14, an extra-cardiovascular electrical stimulation and sensing lead 16 coupled to ICD 14, and an intra-cardiac pacemaker 100. ICD 14 and pacemaker 100 may be enabled to communicate via TCC for transmitting a variety of data or commands. For example, ICD 14 and pacemaker 100 may be configured to communicate via TCC to confirm detected cardiac events or a detected heart rhythm and/or coordinate delivery of cardiac pacing pulses for bradycardia pacing, ATP therapy, cardioversion/defibrillation (CV/DF) shocks, post-shock pacing, cardiac resynchronization therapy (CRT) or other electrical stimulation therapies in response to an abnormal heart rhythm being detected by one or both of the IMDs 14 and 100.

IMD system 10 senses cardiac electrical signals, such as R-waves attendant to ventricular depolarizations and/or P-waves attendant to atrial depolarizations, for detecting abnormal heart rhythms with high sensitivity and specificity to enable IMD system 10 to deliver (or withhold) appropriate therapies at appropriate times. Transmission of TCC signals by an IMD, e.g., by ICD 14 or pacemaker 100, may cause interference with the sensing circuitry of the transmitting IMD, resulting in false sensing of a cardiac event. Such false sensing of cardiac events due to TCC interference with a cardiac event detector included in electrical signal sensing circuitry may lead to withholding a pacing pulse when a pacing pulse is actually needed or contribute to false detection of a tachyarrhythmia event. The TCC signal transmission techniques disclosed herein reduce the likelihood of a TCC signal being falsely detected as a cardiac event by a cardiac electrical signal sensing circuit of the transmitting device.

The TCC signal transmission techniques may also reduce the likelihood that another IMD implanted in patient 12 that is configured to sense electrophysiological signals, such as R-waves and/or P-waves, falsely senses TCC signals as physiological signals. Another IMD implanted in patient 12 may be the intended receiving device of the transmitted TCC signals, e.g., pacemaker 100 receiving signals from ICD 14 or vice versa. In other cases, another IMD co-implanted in patient 12 may not be the intended receiving device of transmitted TCC signals but may be configured to sense electrophysiological signals via electrodes coupled to the co-implanted IMD. A voltage signal may develop across sensing electrodes of the intended or unintended receiving device that may interfere with electrophysiological sensing and event detection. The TCC signal transmission techniques of the present disclosure may reduce or eliminate the incidence of TCC signals being sensed as electrophysiological signals by any other IMD implanted in patient 12 or an external device having electrodes coupled to the patient externally.

FIG. 1 is described in the context of an IMD system 10 including ICD 14 and pacemaker 100 capable of sensing cardiac electrical signals produced by the patient's heart 8 and delivering cardioversion and/or defibrillation (CV/DF) shocks and cardiac pacing pulses to the patient's heart 8. In some examples, the TCC communication may be "one-way" communication, e.g., transmission only from ICD 14 to pacemaker 100 or transmission only from pacemaker 100 to ICD 14. In other examples, the TCC communication may be "two-way" communication between ICD 14 and pacemaker 100 such that each of pacemaker 100 and ICD 14 can receive and transmit information. It is recognized that aspects of the TCC signal transmission techniques disclosed herein may be implemented in a variety of IMD systems which may include an ICD, pacemaker, cardiac monitor or other sensing-only device, neurostimulator, drug delivery device or other implantable medical device(s). The TCC signal transmission techniques disclosed herein may be implemented in any IMD system that requires communication between one IMD and at least one other medical device, implanted or external. Moreover, the techniques described herein may be utilized by two external devices that communicate using TCC. The techniques may also have non-medical applications as well for devices that are implanted and/or external and communicate using TCC.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). In other instances, the housing 15 of ICD 14 may include a plurality of electrodes on an outer portion of the housing. The outer portion(s) of the housing 15 functioning as an electrode(s) may be coated with a material, such as titanium nitride for reducing post-stimulation polarization artifact. Housing 15 may be used as an active can electrode for use in delivering CV/DF shocks or other high voltage pulses delivered using a high voltage therapy circuit. In other examples, housing 15 may be available for use in delivering relatively lower voltage cardiac pacing pulses and/or for sensing cardiac electrical signals in combination with electrodes carried by lead 16. In any of these examples, housing 15 may be used in a transmitting electrode vector for transmitting TCC signals according to the techniques disclosed herein.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, cardiac electrical signal sensing circuitry, therapy delivery circuitry, TCC transmitting and receiving circuitry, power sources and other components for sensing cardiac electrical signals, detecting a heart rhythm, and controlling and delivering electrical stimulation pulses to treat an abnormal heart rhythm and for transmitting TCC signals to pacemaker 100 and/or receiving TCC signals from pacemaker 100.

Lead 16 includes an elongated lead body 18 having a proximal end 27 that includes a lead connector (not shown) configured to be connected to ICD connector assembly 17 and a distal portion 25 that includes one or more electrodes. In the example illustrated in FIG. 1, the distal portion 25 of lead body 18 includes defibrillation electrodes 24 and 26 and pace/sense electrodes 28 and 30. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be selectively activated independently.

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to pacing and sensing electrodes 28 and 30. However, electrodes 24 and 26 and housing 15 may also be utilized to provide pacing functionality, sensing functionality, and/or TCC signal transmission and receiving in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, electrodes 24 and 26 may be used in a sensing vector used to sense cardiac electrical signals and detect and discriminate tachyarrhythmias. Electrodes 24 and 26 may be used in a TCC signal transmission vector in combination with each other, collectively with housing 15, or individually with housing 15. In the case of ICD 14 being configured to receive TCC signals from pacemaker 100, electrodes 24, 26 and/or housing 15 may be used in a TCC receiving electrode vector. The transmitting and receiving electrode vectors may be the same or different vectors.

Electrodes 28 and 30 are relatively smaller surface area electrodes which are available for use in sensing electrode vectors for sensing cardiac electrical signals and may be used for delivering relatively low voltage pacing pulses in some configurations. Electrodes 28 and 30 are referred to as pace/sense electrodes because they are generally configured for use in low voltage applications, e.g., delivery of relatively low voltage pacing pulses and/or sensing of cardiac electrical signals, as opposed to delivering high voltage cardioversion defibrillation shocks. In some instances, electrodes 28 and 30 may provide only pacing functionality, only sensing functionality or both. Furthermore, one or both of electrodes 28 and 30 may be used in TCC signal transmission and/or receiving in some examples.

ICD 14 may obtain cardiac electrical signals corresponding to electrical activity of heart 8 via a combination of sensing electrode vectors that include combinations of electrodes 24, 26, 28, 30 and/or housing 15. Various sensing electrode vectors utilizing combinations of electrodes 24, 26, 28, and 30 may be selected by sensing circuitry included in ICD 14 for receiving a cardiac electrical signal via one or more sensing electrode vectors.

In the example illustrated in FIG. 1, electrode 28 is located proximal to defibrillation electrode 24, and electrode 30 is located between defibrillation electrodes 24 and 26. Electrodes 28 and 30 may be ring electrodes, short coil electrodes, hemispherical electrodes, or the like. Electrodes 28 and 30 may be positioned at other locations along lead body 18 and are not limited to the positions shown. In other examples, lead 16 may include none, one or more pace/sense electrodes and/or one or more defibrillation electrodes.

A TCC transmitting electrode vector may be selected from defibrillation electrodes 24, 26, 28, 30 and housing 15 for transmitting TCC signals produced by a TCC transmitter included in ICD 14. Electrodes, such as defibrillation electrodes 24 and 26 and housing 15, having a relatively large surface area may be used to transmit TCC signals to minimize the impedance of the transmitting electrode vector. A low impedance of the transmitting electrode vector maximizes the injected current signal.

The TCC transmitting electrode vector may be selected to minimize impedance of the transmitting electrode vector and maximize transimpedance from the transmitting electrode vector to the intended receiving electrode vector. As used herein, the term "transimpedance" refers to the voltage received at a TCC signal receiving electrode vector divided by the transmitted current (voltage out divided by current in). As such, the transimpedance for a given TCC communication electrode vector for each of two IMDs configured to communicate bidirectionally is the same for communication in both directions for a given set of transmitting and receiving electrode vectors. By maximizing transimpedance, the voltage signal at the intended receiving electrodes is maximized for a given current signal injected in the tissue conductance pathway. As such, a low impedance of the transmitting electrode vector and high transimpedance of the TCC pathway increases the received TCC signal strength (voltage signal) at the receiving electrode vector.

Among the factors that may contribute to a maximized transimpedance of the TCC pathway are a substantially parallel electrical configuration of the transmitting and receiving electrode configuration, relatively wide spacing of the transmitting electrodes, relatively wide spacing of the receiving electrodes, and close proximity of the transmitting electrode vector to the receiving electrode vector. A transmitting electrode vector closer in proximity to the receiving electrode vector improves the strength of the TCC signal compared to a larger separation of the transmitting and receiving electrode vectors. The optimal orientation for the receiving electrode vector is parallel to the conductive tissue pathway of the current flow. A transmitting electrode vector that is substantially electrically parallel to the receiving electrode vector improves the strength of the TCC signal compared to the receiving electrode vector being orthogonal to the pathway of the current flow through the body tissue, which may result in a null signal.

A parallel electrical configuration between the transmitting and receiving electrode vectors may coincide with physically parallel electrode pairs. The physical electrode vectors may be viewed in some cases as the line the extends from one electrode of the vector to the other electrode of the vector to determine orientation of the transmitting and received vectors relative to one another. In some instances, however, physically parallel electrode pairs may not be electrically parallel depending on the electrical conduction properties of the intervening tissues. For example, a body tissue having relatively low electrical conductance, such as lung tissue, compared to other surrounding tissues, may require a physical electrode configuration that is not necessarily parallel in order to achieve an electrical configuration that is substantially parallel.

The TCC transmitting electrode vector may be selected to include electrodes that are not coupled to ICD sensing circuitry, e.g., a cardiac event detector configured to sense R-waves and/or P-waves from an electrical signal received by a sensing electrode vector. Use of an electrode for TCC signal transmission that is also coupled to a cardiac electrical event detector or other electrical signal sensing circuitry may increase interference with cardiac event detection or other electrical signal monitoring. The transmitting electrode pair may be selected to include at least one or both electrodes that are not coupled to the cardiac electrical event detector of ICD 14 so that TCC signals that are unintentionally received by the cardiac event detector are received via a transimpedance pathway from the transmitting electrode vector to the sensing electrode vector rather than directly through the sensing electrode impedance.

In other examples, however, the TCC transmitting electrode vector may include one or more electrodes coupled to cardiac electrical event detector included in ICD 14. A transmitting electrode vector may include electrodes coupled to the ICD sensing circuitry when the resulting transmitting electrode vector is optimal in other ways, e.g., low impedance and high transimpedance. Transmission of TCC signals using one or both electrodes included in a sensing electrode vector coupled to a cardiac event detector may be selected in a trade-off for optimizing other considerations in achieving reliable TCC signal transmission and reception. TCC signal transmission techniques disclosed herein may reduce or eliminate interference of the TCC signal transmission with cardiac event (or other electrophysiological signal) sensing as well as other sensing functions such as electrical impedance monitoring of a medical electrical lead or body tissue.

In one example, defibrillation electrode 24 may be selected in combination with housing 15 for transmitting TCC signals to pacemaker 100. In other examples, TCC signals may be transmitted by ICD 14 using defibrillation electrode 26 and housing 15 or using two defibrillation electrodes 24 and 26. The transmitting electrode vector impedance (delivered voltage divided by delivered current)

may be up to hundreds of ohms. The transimpedance of the TCC pathway that includes a transmitting electrode vector including one defibrillation electrode 24 or 26 paired with housing 15 may be less than 10 ohms and even less than 1 ohm. A high transimpedance at the TCC signal transmission frequency is desired to produce a relatively high voltage on the receiving electrodes for a given injected current of the TCC signal.

The electrode pair selected for transmitting TCC signals may include one or both of pace/sense electrodes 28 and 30 in some examples. For example, the pace/sense electrode 28 or 30 may be paired with housing 15, defibrillation electrode 24 or defibrillation electrode 26 for transmitting TCC signals. The impedance of the transmitting electrode vector may be increased due to the relatively smaller surface area of pace/sense electrodes 28 and 30, which may have the effect of lowering the injected current during TCC signal transmission and thereby lowering the received voltage signal at the receiving electrode vector.

ICD 14 may be configured to select a TCC transmitting electrode vector from among multiple possible vectors using electrodes 24, 26, 28, 30 and housing 15 to achieve the best TCC signal strength at the receiving electrodes of pacemaker 100 and/or minimize TCC signal interference with cardiac event detection, impedance monitoring, or other functions performed by the ICD sensing circuit and/or by a sensing circuit of pacemaker 100. In some examples, multiple vectors may be used to transmit TCC signals to cover different angles in three-dimensional space to achieve at least one TCC transmitting electrode vector that is substantially electrically parallel to the receiving electrode vector. The electrical configuration of a single transmitting vector relative to the TCC receiving vector may be time-varying due to heart motion when the receiving electrode vector is within or coupled to the patient's heart, as in the case of pacemaker 100.

In the example shown, lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum or substernally under the ribcage and/or sternum 22. Although illustrated in FIG. 1 as being offset laterally from and extending substantially parallel to sternum 22, the distal portion 25 of lead 16 may be implanted at other locations, such as over sternum 22, offset to the right or left of sternum 22, angled laterally from sternum 22 toward the left or the right, or the like. Alternatively, lead 16 may be placed along other subcutaneous, submuscular or substernal paths. The path of extra-cardiovascular lead 16 may depend on the location of ICD 14, the arrangement and position of electrodes carried by the lead body 18, and/or other factors.

Electrical conductors (not illustrated) extend through one or more lumens of the elongated lead body 18 of lead 16 from the lead connector at the proximal lead end 27 to electrodes 24, 26, 28, and 30 located along the distal portion 25 of the lead body 18. The elongated electrical conductors contained within the lead body 18 are each electrically coupled with respective defibrillation electrodes 24 and 26 and pace/sense electrodes 28 and 30, which may be separate respective insulated conductors within the lead body 18. The respective conductors electrically couple the electrodes 24, 26, 28, and 30 to circuitry of ICD 14, such as a signal generator for therapy delivery and TCC signal transmission and/or a sensing circuit for sensing cardiac electrical signals and/or receiving TCC signals, via connections in the connector assembly 17, including associated electrical feedthroughs crossing housing 15.

The electrical conductors transmit therapy from a therapy delivery circuit within ICD 14 to one or more of defibrillation electrodes 24 and 26 and/or pace/sense electrodes 28 and 30 and transmit sensed electrical signals from one or more of defibrillation electrodes 24 and 26 and/or pace/sense electrodes 28 and 30 to the sensing circuit within ICD 14. The electrical conductors also transmit TCC signals from a signal generator to electrodes selected for transmitting the TCC signals. In some examples, ICD 14 may receive TCC signals from pacemaker 100 in which case the TCC signals are conducted from a receiving pair of electrodes of ICD 14 to a TCC signal receiver enclosed by housing 15.

The lead body 18 of lead 16 may be formed from a non-conductive material and shaped to form one or more lumens within which the one or more conductors extend. Lead body 18 may be a flexible lead body that conforms to an implant pathway. In other examples, lead body 18 may include one or more preformed curves. Various example configurations of extra-cardiovascular leads and electrodes and dimensions that may be implemented in conjunction with the TCC transmission techniques disclosed herein are described in pending U.S. Publication No. 2015/0306375 (Marshall, et al.) and pending U.S. Publication No. 2015/0306410 (Marshall, et al.), both of which are incorporated herein by reference in their entirety.

ICD 14 analyzes the cardiac electrical signals received from one or more sensing electrode vectors to monitor for abnormal rhythms, such as bradycardia, tachycardia or fibrillation. ICD 14 may analyze the heart rate and morphology of the cardiac electrical signals to monitor for tachyarrhythmia in accordance with any of a number of tachyarrhythmia detection techniques. ICD 14 generates and delivers electrical stimulation therapy in response to detecting a tachyarrhythmia, e.g., ventricular tachycardia (VT) or ventricular fibrillation (VF), using a therapy delivery electrode vector which may be selected from any of the available electrodes 24, 26, 28 30 and/or housing 15. ICD 14 may deliver ATP in response to VT detection, and in some cases may deliver ATP prior to a CV/DF shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15. ICD 14 may generate and deliver other types of electrical stimulation pulses such as post-shock pacing pulses or bradycardia pacing pulses using a pacing electrode vector that includes one or more of the electrodes 24, 26, 28, and 30 and the housing 15 of ICD 14.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally.

Pacemaker 100 is shown as a leadless intracardiac pacemaker configured to receive TCC signals from ICD 14 via housing-based electrodes in the examples presented herein and may be configured to transmit TCC signals via housing-based electrodes to ICD 14. Pacemaker 100 may be delivered transvenously and anchored by a fixation member at an intracardiac pacing and sensing site. For example, pacemaker 100 may be implanted in an atrial or ventricular chamber of the patient's heart. In further examples, pacemaker 100 may be attached to an external surface of heart 8 (e.g., in contact with the epicardium) such that pacemaker 100 is disposed outside of heart 8.

Pacemaker 100 is configured to deliver cardiac pacing pulses via a pair of housing-based electrodes and may be configured to sense cardiac electrical signals for determining the need and timing of a delivered pacing pulse. For example, pacemaker 100 may deliver bradycardia pacing pulses, rate responsive pacing pulses, ATP, post-shock pacing pulses, CRT, and/or other pacing therapies. Pacemaker 100 may include a TCC receiver that receives and demodulates TCC signals transmitted from ICD 14 via housing-based electrodes. Pacemaker 100 may include a TCC transmitter that transmits TCC signals to ICD 14 via the housing-based electrodes. Pacemaker 100 is described in greater detail below in conjunction with FIGS. 3A and 3B. An example intracardiac pacemaker that may be included in an IMD system employing TCC is described in U.S. Pat. No. 8,744,572 (Greenhut et al.) incorporated herein by reference in its entirety.

In some examples, pacemaker 100 may be implanted. In the right atrium, the right ventricle or the left ventricle of heart 8 to sense electrical activity of heart 8 and deliver pacing therapy. In other examples, system 10 may include two or more intracardiac pacemakers 100 within different chambers of heart 8 (e.g., within the right atrium, the right ventricle, and/or left ventricle). ICD 14 may be configured to transmit TCC signals to one or more pacemakers implanted within the patient's heart 8 to coordinate electrical stimulation therapy delivery. For example, ICD 14 may transmit command signals to cause pacemaker 100 to deliver a cardiac pacing pulse, ATP therapy, or request confirmation of sensed cardiac electrical events or a tachyarrhythmia detection.

An external device 40 is shown in telemetric communication with ICD 14 by a wireless communication link 42 and pacemaker 100 via a wireless communication link 44. External device 40 may include a processor, display, user interface, telemetry unit and other components for communicating with ICD 14 and pacemaker 100 for transmitting and receiving data via communication link 42 and 44, respectively. Communication link 42 or 44 may be established between ICD 14 or pacemaker 14, respectively, and external device 40 using a radio frequency (RF) link such as BLUETOOTH®, Wi-Fi, or Medical Implant Communication Service (MICS) or other RF or communication frequency bandwidth. In some examples, ICD 14 or pacemaker 100 may communicate with an external device 40 using TCC, e.g., using receiving surface electrodes coupled to external device 40 that are placed externally on patient 12.

External device 40 may be embodied as a programmer used in a hospital, clinic or physician's office to retrieve data from ICD 14 and to program operating parameters and algorithms in ICD 14 for controlling ICD functions. External device 40 may be used to program cardiac event sensing parameters (e.g., R-wave sensing parameters), cardiac rhythm detection parameters (e.g., VT and VF detection parameters) and therapy control parameters used by ICD 14. Data stored or acquired by ICD 14, including physiological signals or associated data derived therefrom, results of device diagnostics, and histories of detected rhythm episodes and delivered therapies, may be retrieved from ICD 14 by external device 40 following an interrogation command. External device 40 may alternatively be embodied as a home monitor or hand-held device, such as a smart phone, tablet or other hand-held device.

In some examples, pacemaker 100 is not capable of bidirectional communication with external device 40. ICD 14 may operate as a control device and pacemaker 100 as a responder. Pacemaker 100 may receive TCC communication signals from ICD 14 that include operating control data and commands (which may be transmitted from external device 40 to ICD 14) so that RF telemetry circuitry need not be included in pacemaker 100. Pacemaker 100 may transmit data, such as information related to delivered pacing therapy and/or acquired cardiac electrical signals on command from ICD 14 via TCC transmissions, and ICD 14 may transmit data received from pacemaker 100 to external device 40 via RF communication. Alternatively, pacemaker 100 may periodically transmit data to ICD 14, which stores it until receiving a request from external device 40.

Figure 2:
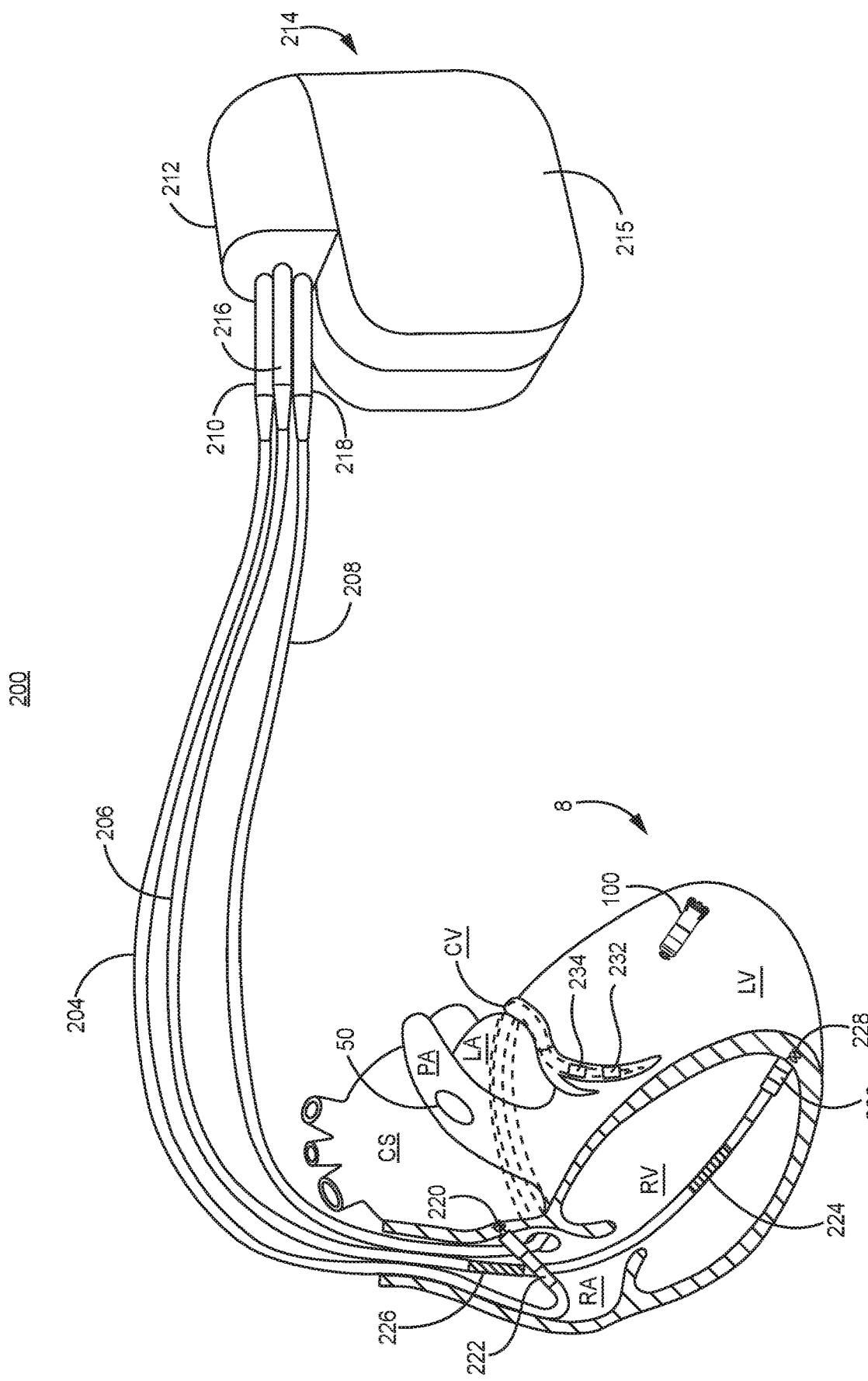
FIG. 2 is a conceptual diagram of an IMD system configured to communicate using TCC techniques disclosed herein according to another example.

FIG. 2 is a conceptual diagram of an IMD system 200 configured to communicate using TCC transmission techniques disclosed herein according to another example. The IMD system 200 of FIG. 2 includes an ICD 214 coupled to a patient's heart 8 via transvenous electrical leads 204, 206, and 208. IMD system 200 may include a leadless pacemaker 100 and/or a leadless sensor 50. Sensor 50 is shown as a leadless pressure sensor positioned in the pulmonary artery for monitoring pulmonary arterial pressure. Leadless pressure sensor 50, also referred to herein as "pressure sensor" 50, may be positioned at other intracardiac or arterial locations for monitoring blood pressure. In other examples, the IMD system 200 (or IMD system 10 of FIG. 1) may include other wireless sensors performing sensing-only or monitoring-only functions configured to send and/or receive TCC signals to/from ICD 214 (or ICD 14 of FIG. 1) and/or pacemaker 100 including, for example, an electrogram (EGM) monitor, an electrocardiogram (ECG) monitor, an oxygen monitor, acoustical monitor, accelerometer, pH monitor, temperature monitor, insulin monitor, or other sensing device including one or any combination of sensors.

ICD 214 includes a connector block 212 that may be configured to receive the proximal ends of a right atrial (RA) lead 204, a right ventricular (RV) lead 206 and a coronary sinus (CS) lead 208, which are advanced transvenously for positioning electrodes for sensing and stimulation in three or all four heart chambers. RV lead 206 is positioned such that its distal end is in the right ventricle for sensing RV cardiac signals and delivering pacing or shocking pulses in the right ventricle. For these purposes, RV lead 206 is equipped with pacing and sensing electrodes shown as a tip electrode 228 and a ring electrode 230. RV lead 206 is further shown to carry defibrillation electrodes 224 and 226, which may be elongated coil electrodes used to deliver high voltage CV/DF pulses. Defibrillation electrode 224 may be referred to herein as the "RV defibrillation electrode" or "RV coil electrode" because it may be carried along RV lead 206 such that it is positioned substantially within the right ventricle when distal pacing and sensing electrodes 228 and 230 are positioned for pacing and sensing in the right ventricle. Defibrillation electrode 226 may be referred to herein as a "superior vena cava (SVC) defibrillation electrode" or "SVC coil electrode" because it may be carried along RV lead 206 such that it is positioned at least partially along the SVC when the distal end of RV lead 206 is advanced within the right ventricle.

Each of electrodes 224, 226, 228 and 230 are connected to a respective insulated conductor extending within the body of RV lead 206. The proximal end of the insulated conductors are coupled to corresponding connectors carried by proximal lead connector 216, e.g., a DF-4 connector, for providing electrical connection to ICD 214. It is understood that although ICD 214 is illustrated in FIG. 2 as a multi-chamber device coupled to RA lead 204 and CS lead 208 in addition to RV lead 206, ICD 214 may be configured as a dual-chamber coupled to only two transvenous leads or a single-chamber device coupled to only one transvenous lead. For example, ICD 214 may be a single-chamber device coupled to RV lead 206 and may be configured to perform the TCC techniques disclosed herein using electrodes 224, 226, 228, and 230 and/or housing 215 in addition to receiving cardiac electrical signals from heart 8 and delivering electrical stimulation therapy to heart 8.

RA lead 204 is positioned such that its distal end is in the vicinity of the right atrium and the superior vena cava. Lead 204 is equipped with pacing and sensing electrodes 220 and 222, shown as a tip electrode 220 and a ring electrode 222 spaced proximally from tip electrode 220. The electrodes 220 and 222 provide sensing and pacing in the right atrium and are each connected to a respective insulated conductor with the body of RA lead 206. Each insulated conductor is coupled at its proximal end to a connector carried by proximal lead connector 210.

CS lead 208 is advanced within the vasculature of the left side of the heart via the coronary sinus (CS) and a cardiac vein (CV). CS lead 208 is shown in FIG. 2 as having one or more electrodes 232, 234 that may be used in delivering pacing and/or sensing cardiac electrical signals in the left chambers of the heart, i.e., the left ventricle and/or the left atrium. The one or more electrodes 232, 234 of CS lead 208 are coupled to respective insulated conductors within the body of CS lead 208, which provide connection to the proximal lead connector 218.

Any of electrodes 220, 222, 224, 226, 228, 230, 232, 234 may be selected by ICD 214 in a TCC electrode vector for transmitting and/or receiving TCC signals. In some examples, housing 215 is selected in a TCC transmission electrode vector along with a lead-based defibrillation electrode, e.g., RV coil electrode 224 or SVC coil electrode 226, to provide a low impedance and high transimpedance TCC transmitting electrode vector. In other examples, TCC transmission is performed using the RV coil electrode 224 and the SVC coil electrode 226. In still other examples, an electrode 232 or 234 carried by the CS lead 208 may be selected in combination with housing 215, RV coil electrode 224, or SVC coil electrode 226. It is recognized that numerous TCC transmission electrode vectors may be available using the various electrodes carried by one or more of leads 204, 206 and 208 coupled to ICD 214. In some examples, multiple vectors may be selected to promote transmission via a vector that is substantially parallel to the housing-based electrodes of pacemaker 100 or to receiving electrodes of leadless pressure sensor 50 for transmitting signals to the respective pacemaker 100 or pressure sensor 50.

Housing 215 encloses internal circuitry generally corresponding to the various modules and components described in conjunction with FIG. 5 below, for sensing cardiac signals from heart 8, detecting arrhythmias, controlling therapy delivery and performing TCC with pacemaker 100 and/or pressure sensor 50 using the techniques disclosed herein. It is recognized that these TCC transmission techniques may be practiced in conjunction with alternative lead and electrode configurations other than those depicted in the examples of FIG. 1 and FIG. 2.

Pressure sensor 50 may be implanted in the pulmonary artery of the patient for monitoring the pulmonary arterial pressure as an indication of the hemodynamic status of the patient 12. One example of pressure sensor 50 is described below in conjunction with FIG. 4. Pressure sensor 50 may be configured to receive pressure signals via a pressure sensor and receive TCC signals via a TCC receiver coupled to electrodes carried by pressure sensor 50.

In the examples of FIGS. 1 and 2, two or more IMDs may be co-implanted in a patient and communicate via TCC to enable a system level of functionality such as sharing the detection of arrhythmias between devices, synchronized timing of anti-tachyarrhythmia shocks, ATP, and/or post-shock pacing, optimization of the resources (e.g., battery capacity or processing power) available to each device, or sharing or coordination of physiological signal acquisition. In some examples, communication between the ICD 14 or 214 and pacemaker 100 may be used to initiate therapy and/or confirm that therapy should be delivered. Communication between ICD 14 or 214 and pressure sensor 50 may be used to initiate pressure signal acquisition and/or retrieval of pressure signal data from pressure sensor 50. One approach is for ICD 14 or 214 to function as a control device and pacemaker 100 and/or sensor 50 to function as responders. For instance, a TCC signal from ICD 14 or 214 may cause pacemaker 100 to deliver a cardiac pacing pulse or therapy.

In another example, ICD 214 may transmit a TCC command signal to pressure sensor 50 for causing pressure sensor 50 to begin acquiring a pressure signal. Pressure sensor 50 may be configured to transmit pressure signal data via TCC to ICD 214 or to external device 40 (shown in FIG. 1). ICD 214 may transmit a TCC command to pressure sensor 50 to cause pressure sensor 50 to transmit a pressure signal in real time, transmit a pressure signal previously acquired and stored by pressure sensor 50, or transmit pressure data derived from a pressure signal received by pressure sensor 50. In other examples, pressure sensor 50 may be configured to transmit pressure signal data via RF telemetry to ICD 214 and/or to an external device, such as device 40 shown in FIG. 1 in response to a TCC command signal received from ICD 214.

During TCC signal transmission, current is driven through the patient's body tissue between two or more electrodes of the transmitting IMD (e.g., ICD 14 or 214). The current spreads through the patient's body, e.g., through the thorax, producing a potential field. The receiving IMD (e.g., pacemaker 100 or sensor 50 or other implanted or external device) may detect the TCC signal by measuring the potential difference between two of its electrodes, e.g., two housing-based electrodes of pacemaker 100 or sensor 50. Optimally, the receiving electrodes are parallel to the tissue conduction pathway of the injected current to maximize the potential difference developed on the receiving electrode pair. The current injected to transmit the TCC signal is of sufficient amplitude to produce a voltage potential that can be detected by an intended receiving IMD but should at the same time not capture excitable body tissue, e.g., causing unintended stimulation of nerve or muscle tissue, possibly leading to muscle contraction, pain or even cardiac capture. Any unintended stimulation of nerve or muscle tissue also likely increases noise received on the sensing electrodes of a device of system 10 or 200.

In some cases, a co-implanted IMD may be an unintended receiver of the TCC signal. If a co-implanted IMD includes electrodes or is coupled to electrodes for receiving electrical signals, but is not the intended receiver of a TCC signal, a voltage potential may develop across the electrodes of the unintended receiver leading to interference with the normal signal detection functions of the unintended receiver. For example, in system 200, ICD 214 and pressure sensor 50 may be configured to communicate using TCC. Pacemaker 100 may be co-implanted with ICD 214 and pressure sensor 50 but not configured to send or receive TCC signals. A TCC signal transmitted by ICD 214 to pressure sensor 50 may result in voltage developed across the housing-based electrodes of pacemaker 100. Pacemaker 100 may be an unintended receiver of the transmitted TCC signal. The voltage developed across the housing-based electrodes of pacemaker 100 may interfere with a cardiac event detector included in pacemaker 100. In other examples, a subcutaneous cardiac electrical signal monitor having housing-based electrodes for monitoring a subcutaneously-acquired electrocardiogram (ECG) signal, such as the REVEAL LINQ™ Insertable Cardiac Monitor (available from Medtronic, Inc., Minneapolis, Minn., USA) may be implanted in a patient having two other IMDs configured to communicate via TCC, such as ICD 214 and pressure sensor 50. The cardiac electrical signal monitor may be an unintended receiver of TCC signals transmitted between ICD 214 and pressure sensor 50. The methods disclosed herein for transmitting TCC signals may eliminate or minimize interference of TCC signals with electrical signal sensing circuitry of other IMDs or external devices in or on the patient, which may be intended or unintended receivers.

While particular IMD systems 10 and 200, including an ICD 14 or 214, respectively, pacemaker 100 and/or pressure sensor 50 are shown in the illustrative examples of FIGS. 1 and 2, methodologies described herein for TCC transmission may be used with other IMD systems including other types and locations of IMDs as well as other lead and electrode arrangements. For example, an implantable cardiac monitor, such as the REVEAL LINQ™ Insertable Cardiac Monitor, may be utilized as a relay device for leadless pacemaker 100 and/or pressure sensor 50 by receiving data from those devices via TCC and transmitting that data to an external device 40 via RF communication, such as BLUETOOTH™ communication. Generally, this disclosure describes various techniques for transmitting TCC signals by an IMD that includes sensing circuitry for sensing a cardiac electrical signal. The TCC signal transmission techniques reduce the likelihood that a TCC signal is oversensed as a cardiac event by the sensing circuitry of the transmitting device. The TCC transmission techniques may also reduce the likelihood of TCC signal oversensing by sensing circuitry included in another IMD co-implanted with the transmitting device. Another IMD co-implanted with the transmitting device may be the intended receiving device of the TCC signal transmission or another that is not the targeted recipient and may not even be configured to receive and detect TCC communication signals.

Figure 3A:
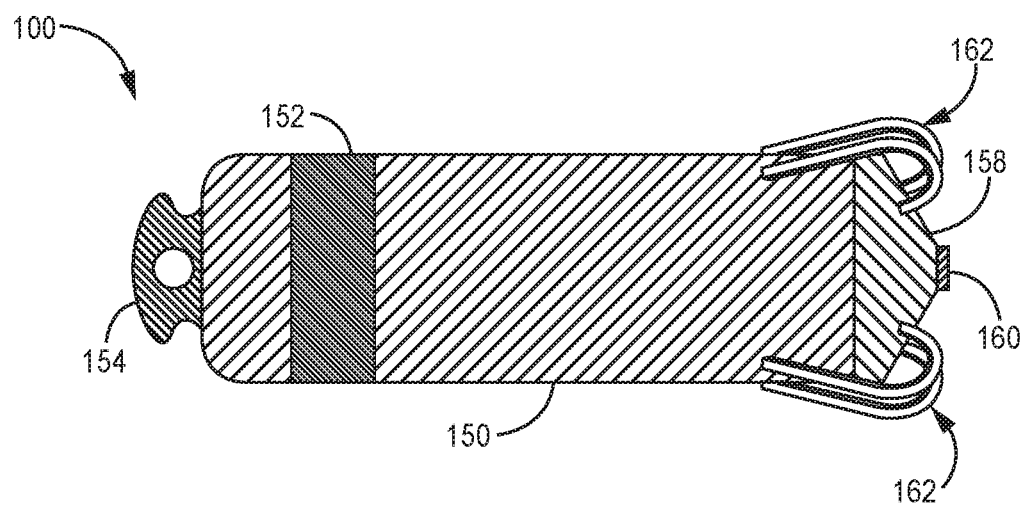
FIG. 3A is a conceptual diagram of a leadless intracardiac pacemaker according to one example.

FIG. 3A is a conceptual diagram of pacemaker 100 according to one example. As shown in FIG. 3A, pacemaker 100 may be a leadless pacemaker including a housing 150, housing end cap 158, distal electrode 160, proximal electrode 152, fixation member 162, and a delivery tool interface member 154. Housing 150, sealed with end cap 158, encloses and protects the various electrical components within pacemaker 100. Pacemaker 100 is shown including two electrodes 152 and 160 but may include two or more electrodes for delivering cardiac electrical stimulation pulses (such as pacing pulses or ATP), sensing cardiac electrical signals for detecting cardiac electrical events, and for receiving and/or transmitting TCC signals.

Electrodes 152 and 160 are carried on the housing 150 and housing end cap 158. In this manner, electrodes 152 and 160 may be considered housing-based electrodes. In other examples, one or more electrodes may be coupled to circuitry enclosed by housing 150 via an electrode extension extending away from housing 150. In the example of FIG. 3A, electrode 160 is disposed on the exterior surface of end cap 158. Electrode 160 may be a tip electrode positioned to contact cardiac tissue upon implantation and fixation at a pacing site by fixation member 162. Electrode 152 may be a ring or cylindrical electrode disposed along the exterior surface of housing 150. Both housing 150 and housing end cap 158 may be electrically insulating. In some examples, housing 150 is an electrically conductive material, e.g., a titanium alloy or other biocompatible metal or metal alloy. Portions of housing 150 may be coated with a non-conductive material, e.g., parylene, polyurethane, silicone or other biocompatible polymer, to insulate portions of housing 150 not functioning as electrode 152.

Electrodes 160 and 152 may be used as a cathode and anode pair for cardiac pacing therapy and receiving and/or transmitting TCC signals. In addition, electrodes 152 and 160 may be used to detect intrinsic electrical signals from the patient's heart 8. In other examples, pacemaker 100 may include three or more electrodes, where any two or more of the electrodes may be selected to form a vector for delivery of electrical stimulation therapy, detecting intrinsic cardiac electrical signals front the patient's heart 8, transmitting TCC signals, and receiving TCC signals. In some examples in which pacemaker 100 includes three or more electrodes, two or more of the electrodes may be selected, e.g., via switches, to form a vector for TCC. Pacemaker 100 may use multiple vectors for TCC transmission or receiving, for example, to promote a substantially parallel electrical configuration with a TCC transmitting electrode vector of ICD 14 or ICD 214, which may increase the transimpedance and increase the received voltage signal.

Fixation member 162 may include multiple tines of a shape memory material that retains a preformed curved shape as shown. During implantation, fixation member 162 may be flexed forward to pierce tissue and elastically flex back towards housing 150 to regain their pre-formed curved shape. In this manner, fixation member 162 may be embedded within cardiac tissue at the implant site. In other examples, fixation member 162 may include helical fixation tines, barbs, hooks or other fixation features.

Delivery tool interface member 154 may be provided for engaging with a delivery tool used to advance pacemaker 100 to an implant site. A delivery tool may be removably coupled to delivery tool interface member 154 for retrieving pacemaker 100 back into a delivery tool if removal or repositioning of pacemaker 100 is required.

Figure 3B:
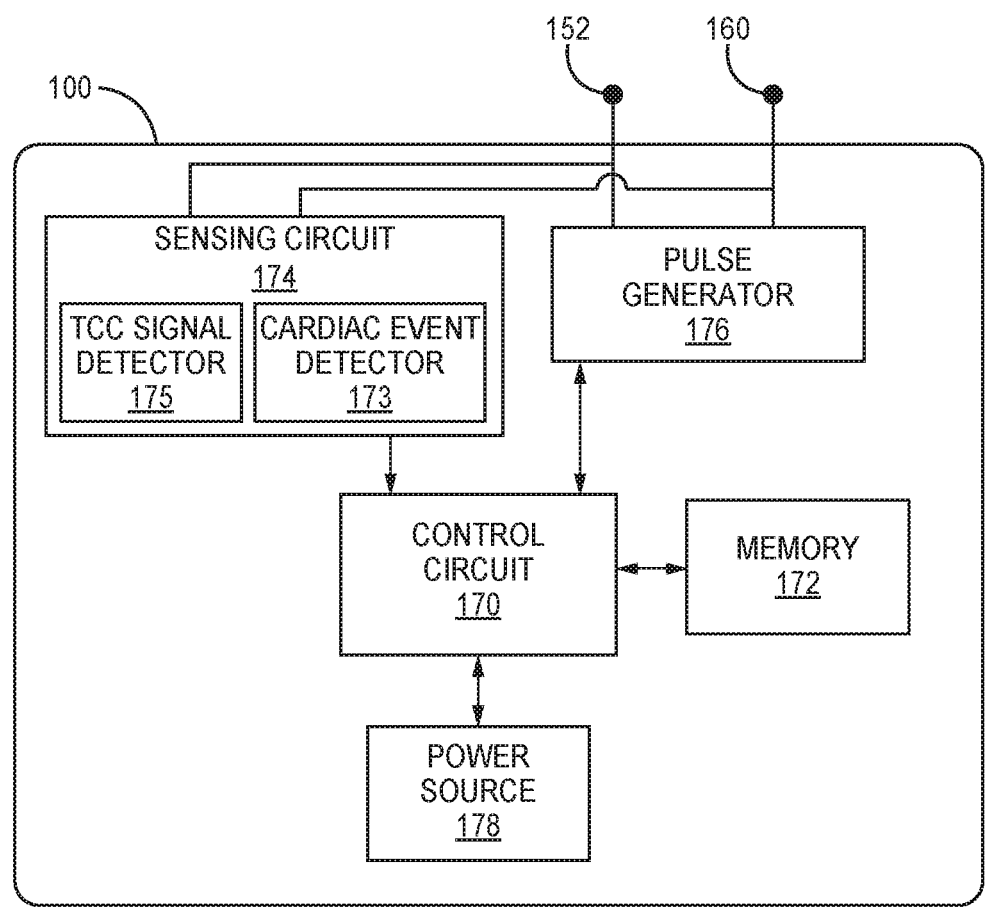
FIG. 3B is a schematic diagram of circuitry that may be included in the pacemaker of FIG. 3A according to one example.

FIG. 3B is a schematic diagram of circuitry that may be enclosed by pacemaker housing 150 according to one example. Pacemaker housing 150 may enclose a control circuit 170, memory 172, pulse generator 176, sensing circuit 174, and a power source 178. Control circuit 170 may include a microprocessor and/or other control circuitry for controlling the functions attributed to pacemaker 100 herein, such as controlling pulse generator 176 to deliver signals via electrodes 152 and 160 and controlling sensing circuit 174 to detect signals from electrical signals received via electrodes 152 and 160. Power source 178 may include one or more rechargeable or non-rechargeable batteries for providing power to control circuit 170, memory 172, pulse generator 176 and sensing circuit 174 as needed. Control circuit 170 may execute instructions stored in memory 172 and may control pulse generator 176 and sensing circuit 174 according to control parameters stored in memory 172, such as various timing intervals, pacing pulse parameters and cardiac event sensing parameters.

Pulse generator 176 generates therapeutic pacing pulses delivered via electrodes 152 and 160 under the control of timing circuitry included in control circuit 170. Pulse generator 176 may include charging circuitry, one or more charge storage devices such as one or more capacitors, and switching circuitry that couples the charge storage device(s) to an output capacitor coupled to electrodes 160 and 152 to discharge the charge storage devices via electrodes 160 and 152. In some examples, pulse generator includes a TCC transmitter (standalone or as part of a transceiver), such as the transmitter described below in conjunction with FIG. 6, for generating TCC signals transmitted via electrodes 160 and 152. Power source 178 provides power to the charging circuit of pulse generator 176 and the TCC transmitter when present.

Pacemaker 100 may be configured for sensing cardiac electrical signals, e.g., R-waves or P-waves, and include a cardiac event detector 173. Intrinsic cardiac electrical events may be detected from an electrical signal produced by the heart and received via electrodes 152 and 160. Cardiac event detector 173 may include filters, amplifiers, an analog-to-digital converter, rectifier, comparator, sense amplifier or other circuitry for detecting cardiac events from a cardiac electrical signal received via electrodes 152 and 160. Under the control of control circuit 170, cardiac event detector 173 may apply various blanking and/or refractory periods to circuitry included in event detector 173 and an auto-adjusting cardiac event detection threshold amplitude, e.g., an R-wave detection threshold amplitude or a P-wave detection threshold amplitude, to the electrical signal received via electrodes 152 and 160.

Sensing circuit 174 may further include a TCC signal detector 175 for detecting a TCC signal from ICD 14 (or ICD 214). A voltage potential may develop across electrodes 152 and 160 in response to current conducted via a tissue pathway during TCC signal transmission from ICD 14 or 214. The voltage signal may be received and demodulated by TCC signal detector 175 and decoded by control circuit 170. TCC signal detector 175 may include amplifiers, filters, analog-to-digital converters, rectifiers, comparators, counters, a phase locked loop and/or other circuitry configured to detect a wakeup beacon signal from a transmitting device and detect and demodulate the modulated carrier signal transmitted in data packets including encoded data. For example, TCC signal detector 175 of pacemaker 100 (and other TCC signal detectors referred to herein) may include a pre-amplifier and a high-Q filter tuned to the carrier frequency of a carrier signal that is used to transmit beacon signals and data signals during a TCC transmission session. The filter may be followed by another amplifier and a demodulator that converts the received signals to a binary signal representing coded data.

The circuitry of TCC signal detector 175 may include circuitry shared with cardiac event detector 173 in some examples. The filters included in TCC signal detector 175 and cardiac event detector 173, however, are expected to operate at different passbands, for example, for detecting different signal frequencies. The TCC signals may be transmitted with a carrier frequency in the range of 33 to 250 kHz, in the range of 60 to 200 kHz, or at 100 kHz as examples. Cardiac electrical signals generated by heart 8 are generally less than 100 Hz. The TCC signal transmission techniques disclosed herein may reduce or eliminate oversensing of a received TCC signal as a cardiac electrical event by cardiac event detector 173. In examples that include a TCC transmitter in pacemaker 100, the TCC signal transmission techniques disclosed herein may reduce or prevent oversensing of a TCC signal produced by pulse generator 176 and transmitted via electrodes 152 and 160 from being detected as a cardiac event by cardiac event detector 173. In some instances, the TCC transmitter may include circuitry shared with pulse generator 176, such that the TCC signals are transmitted using the pacing circuitry of pacemaker 100 and/or transmitted as sub-threshold pacing pulses or pacing pulses that occur during the refractory period of the heart.

In other examples, pacemaker 100 may include fewer or more components than the circuits and components shown in FIG. 3B. For instance, pacemaker 100 may include other physiological sensors and/or an RF telemetry circuit for communication with external device 40 instead of or in addition to TCC signal detector 175 and a TCC transmitter (if included).

Figure 4:
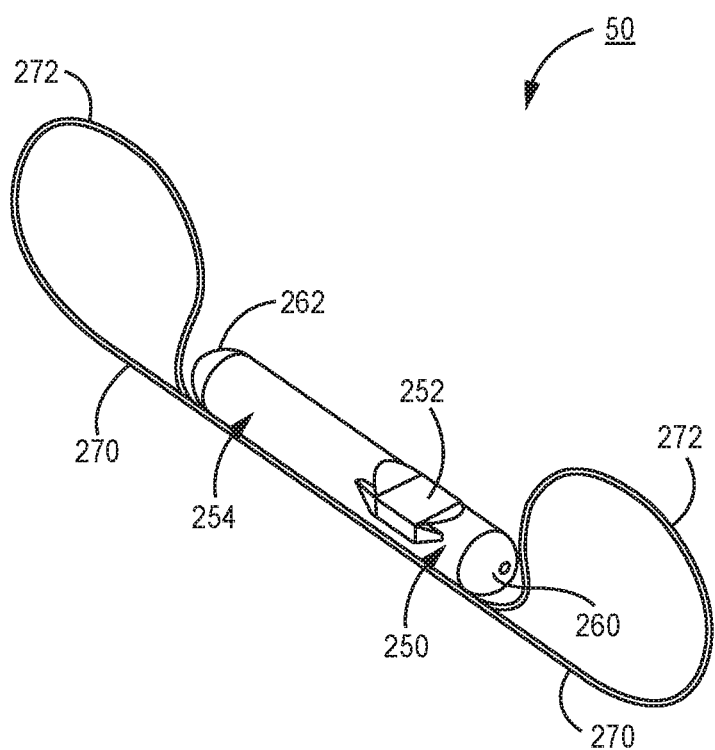
FIG. 4 illustrates a perspective view of a leadless pressure sensor according to one example.

FIG. 4 illustrates a perspective view of leadless pressure sensor 50 according to one example. Leadless pressure sensor 50 may generally correspond to the IMD disclosed in U.S. Pat. Publication No. 2012/0323099 A1 (Mothilal, et al.), incorporated herein by reference in its entirety. As shown in FIG. 4, pressure sensor 50 includes an elongated housing 250 having a pressure sensitive diaphragm or window 252 that exposes a pressure sensitive element within housing 250 to the surrounding pressure. Electrodes 260 and 262 may be secured to opposite ends of housing 250 and may be electrically insulated from housing 250 to form an electrode pair for receiving TCC signals. Electrodes 260 and 262 may be coupled to a TCC signal detector (corresponding to the TCC signal detector 175 described above) enclosed by housing 250. The TCC signal detector is configured to detect and demodulate TCC signals received from ICD 14 or ICD 214.

Housing 250 may enclose a battery, a pressure sensing circuit, a TCC signal detector, control circuitry, and memory for storing pressure signal data. In some examples, the pressure sensing circuit includes an air gap capacitive element and associated circuitry, which may include temperature compensation circuitry, for producing a signal correlated to pressure along window 252. The pressure sensing circuit and window 252 may correspond to a pressure sensor module as generally disclosed in U.S. Pat. No. 8,720,276 (Kuhn, et al.), incorporated herein by reference in its entirety. The pressure sensing circuit may include a micro electro-mechanical system (MEMS) device in some examples. A fixation member 270 extends from housing 250 and may include a self-expanding stent or one or more self-expanding loops 272 that stabilize the position of pressure sensor 50 along an artery, such as the pulmonary artery, by gently pressing against the interior walls of the artery. When deployed in an arterial location, pressure sensor 50 produces and stores pressure signals correlated to arterial blood pressure.

Figure 6:
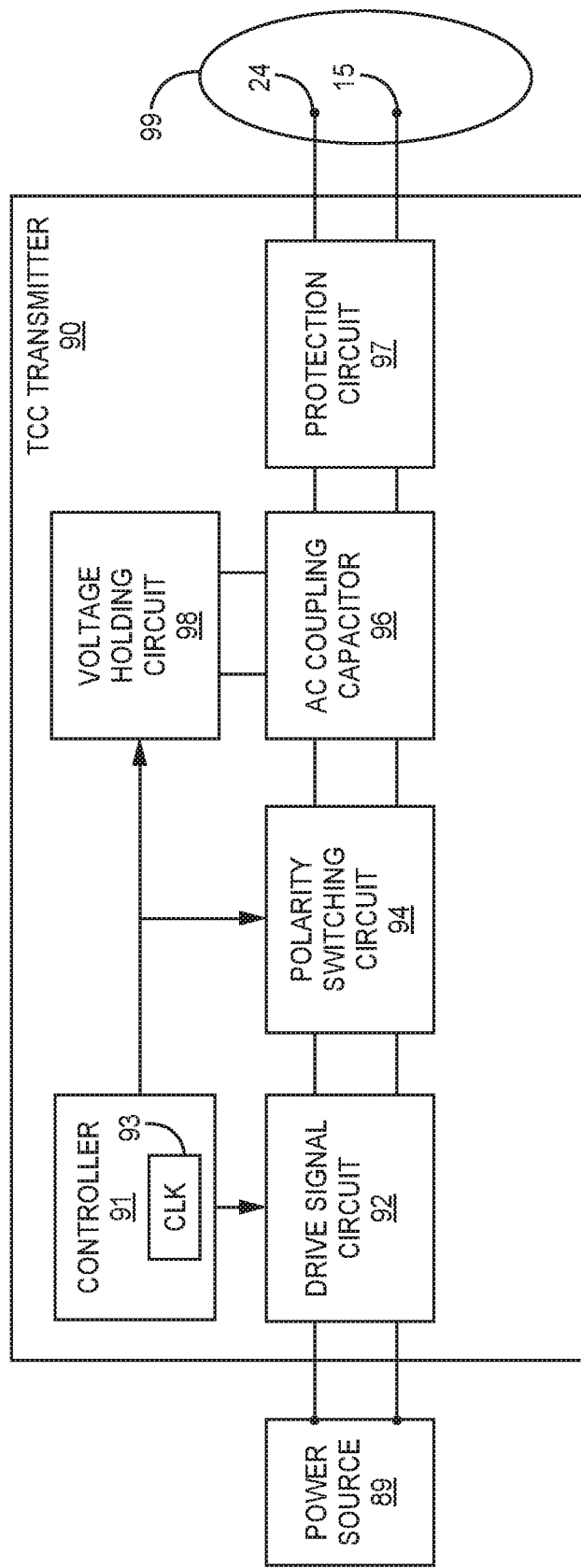
FIG. 6 is a conceptual diagram illustrating an example configuration of a TCC transmitter that may be included in the ICD of FIG. 5 or in the pacemaker of FIG. 3B or pressure sensor of FIG. 4.

In some examples, pressure sensor 50 includes a TCC transmitter, such as the transmitter shown in FIG. 6, for transmitting TCC signals to another medical device, such as ICD 14 or ICD 214, pacemaker 100 or external device 40. Pressure sensor 50 may transmit a pressure signal, data extracted from a pressure signal or other communication data in a TCC signal via electrodes 260 and 262. For instance, pressure sensor 50 may include a TCC transmitter for at least producing acknowledgment and/or confirmation signals transmitted back to a transmitting device, e.g., ICD 14 or ICD 214, in response to receiving a TCC signal to confirm detection of a beacon signal and/or reception of transmitted data packets.

Figure 5:
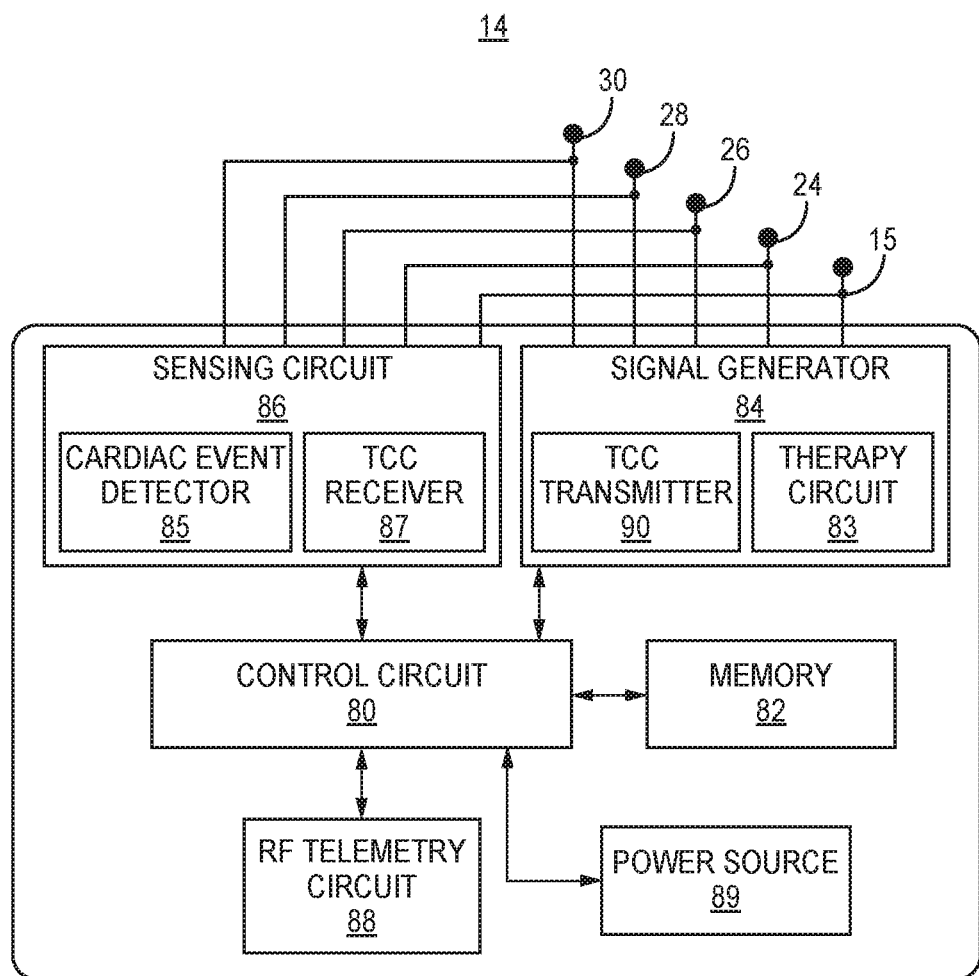
FIG. 5 is a schematic diagram of an ICD capable of transmitting TCC signals according to one example.

FIG. 5 is a schematic diagram of an ICD capable of transmitting TCC signals according to one example. For illustrative purposes, ICD 14 of FIG. 1 is depicted in FIG. 5 coupled to electrodes 24, 26, 28, and 30, with housing 15 represented schematically as an electrode. It is to be understood, however, that the circuitry and components shown in FIG. 5 may generally correspond to circuitry included in ICD 214 of FIG. 2 and adapted accordingly for single, dual, or multi-chamber cardiac signal sensing and therapy delivery functions using electrodes carried by transvenous leads. For instance, in the example of the multi-chamber ICD 214 of FIG. 2, signal generator 84 may include multiple therapy delivery output channels and sensing circuit 86 may include multiple sensing channels each selectively coupled to respective electrodes of RA lead 204, RV lead 206 and CS lead 208, corresponding to each cardiac chamber, e.g., the right atrium, the right ventricle, and the left ventricle.

The ICD circuitry may include a control circuit 80, memory 82, signal generator 84, sensing circuit 86, and RF telemetry circuit 88. A power source 89 provides power to the circuitry of the ICD, including each of the circuits 80, 82, 84, 86, and 88 as needed. Power source 89 may include one or more energy storage devices, such as one or more rechargeable or non-rechargeable batteries. The connections between power source 89 and each of the other circuits 80, 82, 84, 86 and 88 are to be understood from the general block diagram of FIG. 5, but are not shown for the sake of clarity. For example, power source 89 may be coupled to charging circuits included in signal generator 84 for charging capacitors or other charge storage devices included in therapy circuit 85 for producing electrical stimulation pulses such as CV/DF shock pulses or pacing pulses. Power source 89 is coupled to TCC transmitter 90 for providing power for generating TCC signals. Power source 89 provides power to processors and other components of control circuit 80, memory 82, amplifiers, analog-to-digital converters and other components of sensing circuit 86, and a transceiver of RF telemetry circuit 88, as examples.

Memory 82 may store computer-readable instructions that, when executed by a processor included in control circuit 80, cause ICD 14 to perform various functions attributed to ICD 14 (e.g., detection of arrhythmias, communication with pacemaker 100 or pressure sensor 50, and/or delivery of electrical stimulation therapy). Memory 82 may include any volatile, non-volatile, magnetic, optical, or electrical media, such as a random access memory (RAM), read-only memory (ROM), non-volatile RAM (NVRAM), electrically-erasable programmable ROM (EE-PROM), flash memory, or any other digital or analog media.

Control circuit 80 communicates with signal generator 84 and sensing circuit 86 for sensing cardiac electrical activity, detecting cardiac rhythms, and controlling delivery of cardiac electrical stimulation therapies in response to sensed cardiac signals. The functional blocks shown in FIG. 5 represent functionality included in ICD 14 (or ICD 214) and may include any discrete and/or integrated electronic circuit components that implement analog and/or digital circuits capable of producing the functions attributed to ICD 14 herein. Providing software, hardware, and/or firmware to accomplish the described functionality in the context of any modern IMD system, given the disclosure herein, is within the abilities of one of skill in the art.

Sensing circuit 86 may be selectively coupled to electrodes 24, 26, 28, 30 and/or housing 15 in order to monitor electrical activity of the patient's heart 8. Sensing module 86 may include switching circuitry for selecting which of electrodes 24, 26, 28, 30 and housing 15 are coupled to sense amplifiers or other cardiac event detection circuitry included in cardiac event detector 85. Switching circuitry may include a switch array, switch matrix, multiplexer, or any other type of switching device suitable to selectively couple sense amplifiers to selected electrodes. The cardiac event detector 85 within sensing circuit 86 may include one or more sense amplifiers, filters, rectifiers, threshold detectors, comparators, analog-to-digital converters (ADCs), or other analog or digital components configured to detect cardiac electrical events from a cardiac electrical signal received from heart 8.

In some examples, sensing circuit 86 includes multiple sensing channels for acquiring cardiac electrical signals from multiple sensing vectors selected from electrodes 24, 25, 28, 30 and housing 15. Each sensing channel may be configured to amplify, filter, digitize and rectify the cardiac electrical signal received from selected electrodes coupled to the respective sensing channel to improve the signal quality for sensing cardiac events, e.g., P-waves attendant to atrial depolarizations and/or R-waves attendant to ventricular depolarizations. For example, each sensing channel in sensing circuit 86 may include an input or pre-filter and amplifier for receiving a cardiac electrical signal developed across a selected sensing electrode vector, an analog-to-digital converter, a post-amplifier and filter, and a rectifier to produce a filtered, digitized, rectified and amplified cardiac electrical signal that is passed to a cardiac event detector included in sensing circuit 86. The cardiac event detector 85 may include a sense amplifier, comparator or other circuitry for comparing the rectified cardiac electrical signal to a cardiac event sensing threshold, such as an R-wave sensing threshold amplitude, which may be an auto-adjusting threshold. Sensing circuit 86 may produce a sensed cardiac event signal in response to a sensing threshold crossing. The sensed cardiac events, e.g., R-waves and/or P-waves, are used for detecting cardiac rhythms and determining a need for therapy by control circuit 80. ICD 214 of FIG. 2 may include a sensing circuit having a separate atrial sensing channel for sensing P-waves using atrial electrodes and a ventricular sensing channel for sensing R-waves using ventricular electrodes.

Control circuit 80 may include interval counters, which may be reset upon receipt of a cardiac sensed event signal from sensing circuit 86. The value of the count present in an interval counter when reset by a sensed R-wave or P-wave may be used by control circuit 80 to measure the durations of R-R intervals, P-P intervals, P-R intervals and R-P intervals, which are measurements that may be stored in memory 82. Control circuit 80 may use the count in the interval counters to detect a tachyarrhythmia event, such as atrial fibrillation (AF), atrial tachycardia (AT), VF or VT. These intervals may also be used to detect the overall heart rate, ventricular contraction rate, and heart rate variability.

Signal generator 84 includes a therapy circuit 92 and a TCC transmitter 90. The therapy circuit 92 is configured to generate cardiac electrical stimulation pulses, e.g., CV/DF shock pulses and cardiac pacing pulses for delivery to heart 8 via electrodes carried by lead 16 (and in some cases housing 15). Signal generator 84 may include one or more energy storage elements, such as one or more capacitors, configured to store the energy required for a therapeutic CV/DF shock or pacing pulse. In response to detecting a shockable tachyarrhythmia, control circuit 80 controls therapy circuit 83 to charge the energy storage element(s) to prepare for delivering a CV/DF shock. Therapy circuit 83 may include other circuitry, such as charging circuitry, which may include a transformer and/or a charge pump, to charge the energy storage element, and switches to couple the energy storage element to an output capacitor to discharge and deliver the CV/DF shock and change the polarity of the shock to provide a bi-phasic or multi-phasic shock. Therapy circuit 83 may include a variety of voltage level-shifting circuitry, switches, transistors, diodes, or other circuitry. Therapy circuit 83 may include switching circuitry for selecting a shock delivery vector and delivers the shock therapy to the patient's heart 8 via the shock delivery vector, e.g., two or more electrodes such as defibrillation electrode 24 or 26 and housing 15.

In some examples, therapy circuit 83 may include both a low voltage therapy circuit for generating and delivering relatively low voltage therapy pulses, such as pacing pulses, and a high voltage therapy circuit for generating and delivering CV/DF shocks. Low voltage pacing pulses may be delivered via a pacing electrode vector selected from electrodes 24, 26, 28, 30 and housing 15. Pacing pulses may be delivered when a pacing escape interval set by a pace timing circuit of control circuit 80 times out without a sensed cardiac event causing the escape interval to be reset. The pace timing circuit may set various escape intervals for timing pacing pulses, e.g., to provide bradycardia pacing or post-shock pacing, or in response to detecting a tachyarrhythmia by delivering ATP. In some examples, pacemaker 100 is provided for delivering at least some low voltage pacing therapies, e.g., when signaled to do so by a TCC signal transmitted from ICD 14. A low voltage therapy circuit included in ICD 214 of FIG. 2 may include multiple pacing channels, including an atrial pacing channel, a right ventricular pacing channel, and a left ventricular pacing channel, to provide single, dual or multi-chamber pacing in addition to the high voltage therapy circuit used for delivering CV/DF shocks.

In some examples, ICD 14 (or ICD 214) is configured to monitor the impedance of an electrode vector. For example, signal generator 84 may apply a current drive signal to a pair of electrodes coupled to ICD 14. Sensing circuit 86 may detect the resulting voltage developed across the pair of electrodes. Impedance monitoring may be performed for detecting a lead or electrode issue and for selecting a therapy delivery electrode vector, a TCC transmitting electrode vector, or a sensing electrode vector based at least in part on the lead/electrode impedance. In other examples, ICD 14 or ICD 214 may be configured to monitor bioimpedance in a tissue volume, e.g., thoracic impedance or cardiac impedance, for monitoring a patient condition.

TCC transmitter 90 is configured to generate TCC signals for transmission from a transmitting electrode vector selected from the electrodes 24, 26, 28, 30 and housing 15 via a conductive tissue pathway. TCC transmitter 90 is configured to generate and transmit a TCC signal, e.g., to communicate with pacemaker 100, sensor 50 or another IMD, or an external device 40. In some examples, signal generator 84 includes switching circuitry for selectively coupling TCC transmitter 90 to a selected transmission electrode vector, e.g., using any two or more of electrodes 24, 26, 28 30 and housing 15, e.g., housing 15 and defibrillation electrode 24, for transmission of a TCC signal.

The TCC signal may be transmitted having a carrier signal with a peak-to-peak amplitude and carrier frequency selected to avoid stimulation of excitable tissue of patient 12. In some examples, the carrier frequency of the TCC signal may be 100 kilohertz (kHz) or higher. A TCC signal emitted or received, for example by electrode 24 and housing 15, at a frequency of at least approximately 100 kHz may be less likely to stimulate nearby tissue, e.g., muscles or nerves, or cause pain than lower frequency waveforms. Consequently, a TCC signal having a frequency of at least approximately 100 kHz may have a higher amplitude than a lower frequency signal without causing extraneous nerve or muscle stimulation. A relatively higher amplitude signal may increase the likelihood that pacemaker 100, pressure sensor 50 or another implanted or external device, may receive the TCC signal from ICD 14 (or ICD 214). The peak-to-peak amplitude of the TCC signal may be within a range from approximately 100 microamps to 10 milliamps (mA) or more, such as within a range from approximately 1 mA to approximately 10 mA. In some examples, the amplitude of the TCC signal may be approximately 3 mA. A TCC signal having a frequency of at least approximately 100 kHz and an amplitude no greater than approximately 10 mA may be unlikely to stimulate nearby tissue, e.g., muscles or nerves, or cause pain. For a transmitting electrode vector having an impedance of 200 ohms injecting a current signal having an amplitude of 10 mA peak-to-peak, the voltage signal at the transmitting electrode vector may be 2 Volts peak-to-peak. The voltage developed at the receiving electrode vector may be in the range of 0.1 to 100 millivolts peak-to-peak.

The modulation of the TCC signal may be, as examples, amplitude modulation (AM), frequency modulation (FM), or digital modulation (DM), such as frequency-shift keying (FSK) or phase-shift keying (PSK). In some examples, the modulation is FM toggling between approximately 150 kHz and approximately 200 kHz. In some examples, the TCC signal has a frequency of 150/200 kHz and is modulated using FSK modulation at 12.5 kbps. In the illustrative examples presented herein a TCC signal having a carrier frequency of 100 kHz is modulated to encode data using binary phase shift keying (BPSK). Balanced pulses of opposite polarity may be used to shift the phase of the TCC signal, e.g., by 180 degrees positively or negatively, and balance the charge injected into the body tissue during the phase shift to minimize the likelihood of interfering with cardiac event sensing operations of the cardiac event detector 85. Techniques for BPSK modulation of the TCC carrier signal using charge balanced phase shifts are disclosed in U.S. patent application Ser. No. 16/202,418 (Roberts, et al.) incorporated herein by reference in its entirety. The data modulated on TCC signals, e.g., being sent to pacemaker 100 or pressure sensor 50, may include "wake up" commands, commands to deliver a therapy, and/or commands to collect or send physiological signal data, as examples.

The configuration of signal generator 84 including TCC transmitter 90 illustrated in FIG. 5 may provide "one-way" or unidirectional TCC. Such a configuration may be used if, for example, the ICD 14 is configured as a control device to transmit a command or request to another IMD configured as a responder, e.g., to pacemaker 100 or sensor 50, to provide commands for pacing delivery or pressure signal acquisition, for instance. In some examples, sensing circuit 86 may include a TCC receiver 87 to facilitate "two-way" TCC between the ICD and another IMD. ICD 14 or ICD 214 may be configured to receive confirmation signals from the intended receiving device to confirm that a transmitted TCC signal was successfully received. In other examples, ICD 14 or ICD 214 may receive commands via TCC receiver 87 from another IMD or external device. The TCC receiver 87 may have more sensitivity than an RF telemetry circuit 88, e.g., to compensate for lower signal-to-noise ratio signals from a transmitting device such as pacemaker 100 or sensor 50. For instance, pacemaker 100 may generate relatively low signal-to-noise ratio signals by generating relatively small amplitude signals due to its smaller power source, and/or to avoid stimulation of adjacent cardiac tissue. A modulated or unmodulated carrier signal may be received by TCC receiver 87 via electrodes selectively coupled to sensing circuit 86. TCC receiver 87 may include an amplifier, filter and demodulator to pass the demodulated signal, e.g., as a stream of digital values, to control circuit 80 for decoding of the received signal and further processing as needed.

In other examples, TCC receiver 87 and/or TCC transmitter 90 may be distinct components separate from sensing circuit 86 and signal generator 84, respectively. For example, ICD 14 may include a TCC transceiver that incorporates the circuitry of TCC receiver 87 and/or TCC transmitter 90. In this case, the functionality described with respect to TCC receiver 87 and/or TCC transmitter 90 may be performed via a distinct TCC component instead of being part of sensing circuit 86 and signal generator 84.

Memory 82 may be configured to store a variety of operational parameters, therapy parameters, sensed and detected data, and any other information related to the monitoring, therapy and treatment of patient 12. Memory 82 may store, for example, thresholds and parameters indicative of tachyarrhythmias and/or therapy parameter values that at least partially define delivered anti-tachyarrhythmia shocks and pacing pulses. In some examples, memory 82 may also store communications transmitted to and/or received from pacemaker 100, pressure sensor 50 or another device.

ICD 14 may have an RF telemetry circuit 88 including an antenna and transceiver for RF telemetry communication with external device 40. RF telemetry circuit 88 may include an oscillator and/or other circuitry configured to generate a carrier signal at the desired frequency. RF telemetry circuit 88 further includes circuitry configured to modulate data, e.g., stored physiological and/or therapy delivery data, on the carrier signal. The modulation of RF telemetry signals may be, as examples, AM, FM, or DM, such as FSK or PSK.

In some examples, RF telemetry circuit 88 is configured to modulate the TCC signal for transmission by TCC transmitter 90. Although RF telemetry circuit 88 may be configured to modulate and/or demodulate both RF telemetry signals and TCC signals within the same frequency band, e.g., within a range from approximately 150 kHz to approximately 200 kHz, the modulation techniques for the two signals may be different. In other examples, TCC transmitter 90 includes a modulator for modulating the TCC signal and/or TCC receiver 87 includes a demodulator for modulating the TCC signal rather than RF telemetry circuit 88.

FIG. 6 is a conceptual diagram of TCC transmitter 90 according to one example. TCC transmitter 90 (or transmitter portion of a transceiver) may include a controller 91, drive signal circuit 92, polarity switching circuit 94, alternating current (AC) coupling capacitor 96, protection circuit 97 and voltage holding circuit 98. In other examples, TCC transmitter 90 may include fewer or more components than the circuits and components shown in FIG. 6. ICD power source 89 is shown coupled to TCC transmitter 90 to provide power necessary to generate TCC signals. While the controller 91, drive signal circuit 92, polarity switching circuit 94, AC coupling capacitor 96, protection circuit 97 and voltage holding circuit 98 are shown as discrete circuits by the blocks in FIG. 6, it is recognized that these circuits may include common components or a common circuit may perform the functions attributed to the separate circuit blocks shown in FIG. 6. For example, generating a carrier current signal having a carrier frequency and a peak-to-peak amplitude may be performed by drive signal circuit 92 and/or polarity switching circuit 94 under the control of controller 91.

Controller 91 may include a processor, logic circuitry, data registers, a clock circuit and/or other circuitry or structures for providing the functionality attributed to controller 91 herein. Controller 91 may include a dedicated clock circuit 93 for generating clock signals used to control the frequency of the transmitted TCC signals. In other examples, controller 91 may be implemented within control circuit 80. The clock circuit 93 may be configured to provide a clock signal that may be used to transmit the TCC signal during a transmission session using more than one frequency. For example, TCC transmitter 90 may be configured to provide a clock signal that may be used to transmit the TCC signal using at least three different frequencies, the TCC signal being modulated using FSK during a wakeup mode (e.g., modulating the signal using two different frequencies) and switch to a data transmission mode that includes transmitting data packets using a carrier signal at a third frequency (e.g., modulated using BPSK or other modulation technique) For example, during the wakeup mode a beacon signal may be transmitted using high and low alternating frequencies, which may be centered on the frequency of the carrier signal. The beacon signal may be followed by a request to establish a communication, sometimes referred to as an "OPEN" request or command, transmitted at the carrier frequency. A clock signal generated by clock circuit 93 may be required to enable generation of at least three different frequencies of the TCC signal produced by drive signal circuit 92 and/or polarity switching circuit 94 and passed to AC coupling capacitor 96 in this particular example.

After switching from the wakeup mode to the data transmission mode, the TCC transmitter 90 may be configured to transmit the TCC signal at the carrier frequency, different than the distinct high and low frequencies used during the beacon signal transmission. The carrier signal is modulated using BPSK in one example such that the TCC signals are transmitted using a single frequency during the data transmission mode.

The clock circuit 93 may operate at one clock frequency during the wakeup mode and at another clock frequency during the data transmission mode. For example, clock circuit 93 may be controlled to operate at the lowest possible clock frequency that can be used to generate the high frequency and low frequency cycles of the beacon signal during the wakeup mode to conserve power provided by power source 89. The clock circuit 91 may be configured to operate at a higher frequency for controlling drive signal circuit and/or polarity switching circuit to generate the carrier signal during signal transmission. The clock circuit frequency may be changed between the wakeup and transmission modes under the control of controller 91 using digital trim codes stored in hardware registers.

TCC transmitter 90 is shown coupled to a transmitting electrode vector 99 including defibrillation electrode 24 and housing 15 (of FIG. 1) in this example. It is to be understood that TCC transmitter 90 may be coupled to one or more TCC transmitting electrode vectors selected from any of the available electrodes coupled to the transmitting device as described above, e.g., via switching circuitry included in signal generator 84. Controller 91 may be configured to switchably connect a transmitting electrode vector 99 to TCC transmitter 90 for transmission of TCC signals, e.g., by controlling switches included in signal generator 84, which may be included in TCC transmitter 90 between AC coupling capacitor 96 and transmitting electrode vector 99, e.g., in protection circuit 97. Controller 91 may select a transmitting electrode vector from among multiple electrodes coupled to the transmitting device, which may include electrodes carried by the housing of the transmitting device, a transvenous lead, e.g., any of leads 204, 206 or 208 shown in FIG. 2, or a non-transvenous lead, e.g., extra-cardiovascular lead 16 shown in FIG. 1.

Drive signal circuit 92 may include a voltage source and/or a current source powered by power source 89. In one example, drive signal circuit 92 may be an active drive signal circuit generating a balanced, bi-directional drive current signal to balance the return current with the drive current for a net zero DC current injected into the body tissue via transmitting electrode vector 99. In another example, the drive signal circuit 92 may include a charge pump and a holding capacitor that is charged by the charge pump to generate a current signal that is coupled to the transmitting electrode vector 99. In yet another example, drive signal circuit 92 may include a current source that is used to charge a holding capacitor included in drive signal circuit 92.

The drive signal generated by drive signal circuit 92 may be a voltage signal in some examples. In the illustrative examples presented herein, the drive signal circuit 92 generates a current signal to deliver TCC signal current through the transmitting electrode vector 99 having a desired peak-to-peak amplitude, e.g., high enough to produce a voltage signal on receiving electrodes of a receiving device that is detectable by the receiving device, which may be pacemaker 100, sensor 50 or another intended receiving medical device, implanted or external. The peak-to-peak current amplitude is low enough to avoid or minimize the likelihood of stimulation of tissue. A carrier signal that may be generated by drive signal circuit 92 and/or polarity switching circuit 94 may have a peak-to-peak amplitude in a range from approximately 1 mA to approximately 10 mA, such as approximately 3 mA peak-to-peak, as discussed above. The voltage developed at the receiving electrode vector may be in the range of 0.1 to 100 millivolts peak-to-peak.

Polarity switching circuit 94 receives the drive signal from drive signal circuit 92 and includes circuitry configured to switch the polarity of the drive signal current at a carrier frequency of the TCC signal. For example, polarity switching circuit 94 may include transistors and/or switches configured to switch the polarity of the drive current signal at the frequency of the TCC signal. In some examples, polarity switching circuit includes a respective one or more transistors and/or switches coupled to each of electrode 24 and housing 15, and the on-off states of the respective transistor(s) and/or switch(es) are alternated to switch the polarity of the TCC signal current between the electrodes at the carrier frequency. As discussed above, the carrier frequency may be approximately 100 kHz. For example, the carrier frequency may be within a range from approximately 33 kHz to approximately 250 kHz.

In some examples, RF telemetry module 86 may include a mixed signal integrated circuit or other circuitry configured to provide a digital version of the modulated TCC signal to controller 91. In other examples, controller 91 is configured to produce the digital input signal for modulating the TCC carrier signal to encode communication data in the transmitted signal. Controller 91 controls one or both of drive signal circuit 92 and/or polarity switching circuit 94 to modulate the TCC carrier frequency signal to generate the modulated TCC signal with an amplitude, phase shifts and/or frequency according to the encoding. For example, controller 92 may control polarity switching circuit 94 to toggle the frequency of the carrier signal according to FSK modulation to encode the communication data. In another example, controller 91 may control polarity switching circuit 94 to switch the polarity of the current signal after a desired portion of the carrier frequency cycle length to shift the phase of the AC current signal by 180 degrees according to BPSK modulation.

Polarity switching circuit 94 is capacitively coupled to the transmitting electrode vector 99 (e.g., electrode 24 and housing 15 in the example shown) via AC coupling capacitor 96. AC coupling capacitor 96 couples the current signal output from polarity switching circuit 94 to the transmitting electrode vector 99 to inject the current into the conductive body tissue pathway. AC coupling capacitor 96 may include one or more capacitors coupled in series with one or each of the electrodes included in electrode vector 99. The AC coupling capacitor 96 is charged to a DC operating voltage at the beginning of a TCC signal. AC coupling capacitor 96 is selected to have a minimum capacitance that is based on the frequency and the peak-to-peak current amplitude of the carrier signal being used to transmit beacon and data signals. As examples, AC coupling capacitor 96 may have a capacitance of at least one nanofarad and up to ten microfarads for coupling a carrier signal having a frequency between 25 kHz and 250 kHz and peak-to-peak current amplitude of 100 microamps to 10 milliamps. Larger capacitances may be used but may increase the time required to charge the AC coupling capacitor to a DC operating voltage.

During a "cold start," e.g., at the beginning of a TCC transmission session when AC coupling capacitor 96 is uncharged, the charging of AC coupling capacitor 96 to the DC operating voltage may result in a low frequency current being injected into the body through the transmitting electrode vector. This low frequency current is more likely to interfere with the operation of cardiac event detector 85 or other electrophysiological signal sensing circuits included in co-implanted IMDs or external devices coupled to the patient. Cardiac event detector 85 and other electrophysiological signal sensing circuits of intended or unintended receiving devices may operate in a low frequency band, e.g., 1 to 100 Hz. As such, low frequency artifact at the start of TCC signal transmission, during charging of the AC coupling capacitor 96, may interfere with cardiac event detector 85. After the DC operating voltage is established on AC coupling capacitor 96, the high frequency carrier signal, e.g., 100 kHz, is typically above the operating bandwidth of cardiac event detector 85 and other electrophysiological sensing circuitry of an IMD system and unlikely to cause interference or false event detection.

TCC transmitter 90 includes a voltage holding circuit 98 coupled to AC coupling capacitor 96. Voltage holding circuit 98 is configured to hold the AC coupling capacitor at the DC operating voltage between transmitted TCC signals during a TCC transmission session and/or between TCC transmission sessions. By holding the AC coupling capacitor 96 at a DC voltage during time intervals between TCC signal transmissions, interference with sensing circuitry that may otherwise occur due to the low frequency artifact injected during charging of the AC coupling capacitor 96 to the DC operating voltage is reduced, minimized or avoided.

In one example, voltage holding circuit 98 includes a low leakage storage capacitor and switches for coupling AC coupling capacitor 96 across the storage capacitor between TCC signal transmissions. The storage capacitor may store the charge of AC coupling capacitor 96 between TCC signal transmissions. Voltage holding circuit 98 may include an amplifier for driving the stored voltage from the storage capacitor to the AC coupling capacitor 96 prior to the next TCC signal. Other examples of circuitry included in voltage holding circuit 98 are described below in conjunction with FIGS. 7 and 9. In some examples, voltage holding circuit 98 may include circuitry for floating AC coupling capacitor 96 at the DC voltage between TCC signal transmissions. In other examples, voltage holding circuit 98 may include circuitry to actively hold the AC coupling capacitor 96 at a DC voltage between TCC signal transmissions.

A variety of circuitry may be used for preventing or minimizing discharging of AC coupling capacitor 96 between TCC signal transmissions. In this way, at the start of transmitting the next TCC signal, the AC coupling capacitor 96 is already at or near the DC operating voltage. Without having to re-establish the DC voltage on the AC coupling capacitor 96, low frequency artifact injected into the TCC tissue pathway at the onset of the next TCC signal transmission is reduced, avoided or minimized. It is recognized that leakage currents may still exist within TCC transmitter 90 and may cause some discharge of AC coupling capacitor 96 between signal transmissions. Voltage holding circuit 98 may be used to reduce any discharge of AC coupling capacitor 96 between transmitted TCC signals to reduce low frequency interference with sensing circuit 86 (FIG. 5) of the transmitting device as well as sensing circuits of other co-implanted IMDs and/or external device coupled to the patient.

The TCC transmitter 90 may include protection circuit 97 that allows the delivery of the TCC signal via electrodes coupled to other ICD circuitry but protects the TCC transmitter 90 and other circuitry of the ICD 14 from voltages that may develop across the electrodes, e.g., during a CV/DF shock delivered by therapy circuit 83 or an external defibrillator as well as high voltages that may develop across the TCC transmitting electrode vector during other situations such as an electrocautery procedure or magnetic resonance imaging. The circuitry within housing 1:5 of ICD 14 protected by protection circuit 97 may include circuitry of any of the components of ICD 14 illustrated in FIG. 5, such as control circuit 80, memory 82, sensing circuit 86, signal generator 84, and RF telemetry circuit 88.

Protection circuit 97 may be coupled between drive signal circuit 92 and the transmitting electrode vector 99, e.g., between AC coupling capacitor 96 and electrode 24 and housing 15 as shown. In some examples, protection circuit 97 may include circuitry before and/or after AC coupling capacitor 96. Protection circuit 97 may include, as examples, capacitors, inductors, switches, resistors, and/or diodes. Examples of TCC signal generation and protection circuitry that may be utilized in conjunction with the signal transmission techniques disclosed herein are generally described in U.S. Pat. No. 9,636,511 (Carney, et al.), incorporated herein by reference in its entirety.

In some examples, TCC transmitter 90 may be controlled by control circuit 80 to transmit data via TCC multiple times throughout a cardiac cycle. In some cases, multiple transmissions at different times during the cardiac cycle increase the likelihood that the data is sent during both systole and diastole to make use of cardiac motion to increase the chance that the intended receiving electrode vector, such as housing-based electrodes of pacemaker 100 or pressure sensor 50, is orientated in a non-orthogonal position relative to the transmitting electrode vector. Multiple transmissions at different times during the cardiac cycle may thereby increase the likelihood that that the packet is received. While TCC transmitter 90 is shown coupled to a transmitting electrode bipole (vector 99) in FIG. 6, it is to be understood that multiple transmitting electrode vectors may be coupled to TCC transmitter 90 for transmitting a TCC current signal along multiple conductive tissue pathways for reception by multiple receiving electrode vectors or to increase the likelihood of being received by a single receiving electrode vector.

Figure 7:
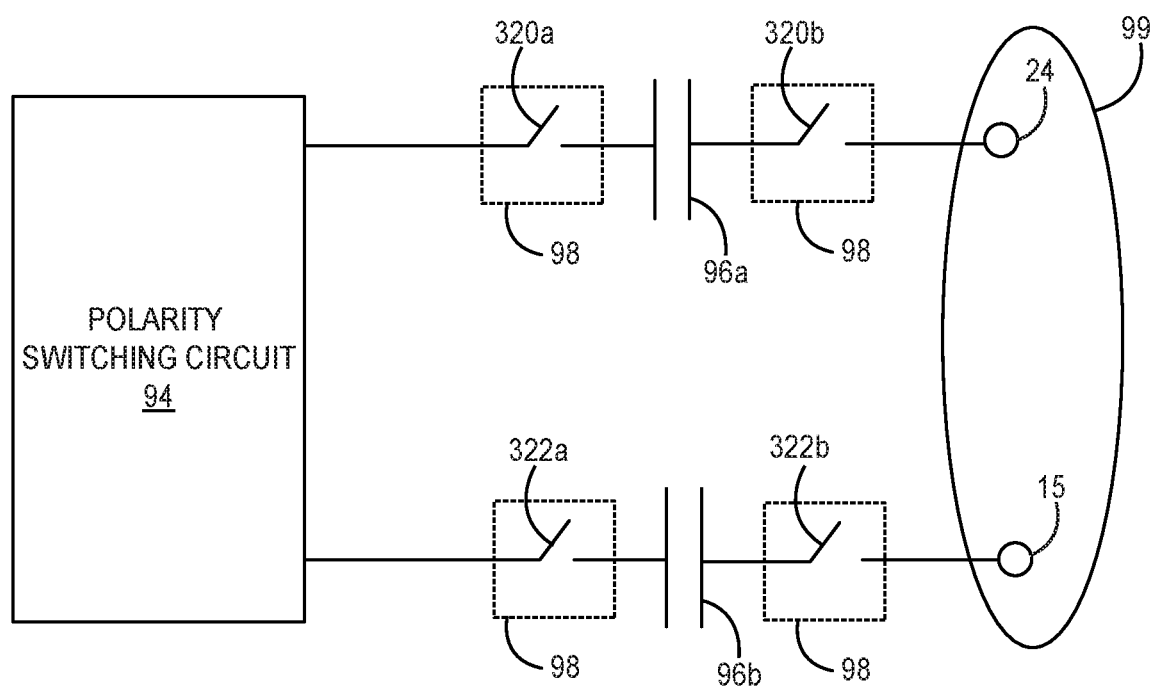
FIG. 7 is a conceptual diagram of circuitry included in the TCC transmitter of FIG. 6, including a voltage holding circuit, according to one example.

FIG. 7 is a conceptual diagram of circuitry included in the TCC transmitter 90 of FIG. 6, including voltage holding circuit 98, according to one example. In this example, AC coupling capacitor 96 includes two capacitors 96a and 96b, each coupled in series with a respective electrode of the transmitting electrode vector 99 (shown as electrode 24 and housing 15 in FIG. 7). The voltage holding circuit 98 may include at least one switch coupled to at least one side of each capacitor 96a and 96b of AC coupling capacitor 96. In the example shown, voltage holding circuit 98 includes four switches 320a, 320b, 322a and 322b so that one switch is provided on each side of the respective coupling capacitors 96a and 96b. The two switches 320a, 320b and 322a, 322b coupled to respective sides of respective capacitors 96a and 96b may be opened to "float" the capacitors 96a and 96b, collectively AC coupling capacitor 96, between transmission of consecutive TCC signals within a TCC transmission session and/or between consecutive TCC transmission sessions. In other examples, the voltage holding circuit 98 may include at least one switch coupled to at least one side of each capacitor 96a and 96b of AC coupling capacitor 96, e.g., such as only including switches 320a, 322a or only including switches 320b and 322b.

Controller 91 may be configured to open switches 320a, 320b, 322a and 322b of voltage holding circuit 98 at the end of a TCC signal transmission to uncouple capacitors 96a and 96b from any current pathways in TCC transmitter 90. Discharge of the DC voltage that was developed on AC coupling capacitor 96, e.g., the two capacitors 96a and 96b, during transmission of the TCC signal is thereby reduced, prevented or minimized. In the example shown, each side of each of the capacitors 96a and 96b is uncoupled from the respective polarity switching circuit 94 or the transmitting electrode vector 99. By opening at least one or both of switches 320a and/or 320b and 322a and/or 322b during periods of time between successive TCC signal transmissions, current paths into and out of AC coupling capacitor 96 are disconnected. A small leakage current may occur through the switches 320a, 320b, 322a and 322b. However, any small loss of the DC voltage across AC coupling capacitor 96 may be quickly re-established at the start of the next TCC signal transmission, reducing any low frequency artifact that may occur. If the time between transmissions of successive TCC signals is relatively short, the leakage current through switches included in voltage holding circuit 98 is minimal, reducing any low frequency artifact at the start of the next TCC signal transmission.

Switches 320a, 320b, 322a and 322b may be MOSFET switches in an integrated circuit with AC coupling capacitor 96 for floating the AC coupling capacitor 96 (which may include one or more capacitors in series with each electrode of the transmitting electrode vector 99 as shown in FIG. 7). The switches 320a, 320b, 322a, and 322b are expected to hold capacitors 96a and 96b at or near (e.g., within a particular range of, such as within 10%, within 5%, within 3% or within 1%) the DC voltage established on each respective capacitor 96a and 96b during transmission of a TCC signal for at least one minute or more without significant voltage loss. As such, voltage holding circuit 98 may be controlled by controller 91 to open switches 320a, 320b, 322a, and 322b at the end of a TCC signal transmission until the start of the next successive TCC signal transmission, which may start up to several seconds, one minute, or even several minutes after the immediately preceding TCC signal transmission. The TCC signals that are transmitted one after another may be successive beacon signals that are transmitted to wake up a receiving device during a wake up mode of the transmitting device, successive data packets transmitted during a data transmission mode of the transmitting device, a beacon signal followed by a data packet, or the last data packet of one transmission session followed by the first beacon signal of the next transmission session, as examples.

Figure 8:
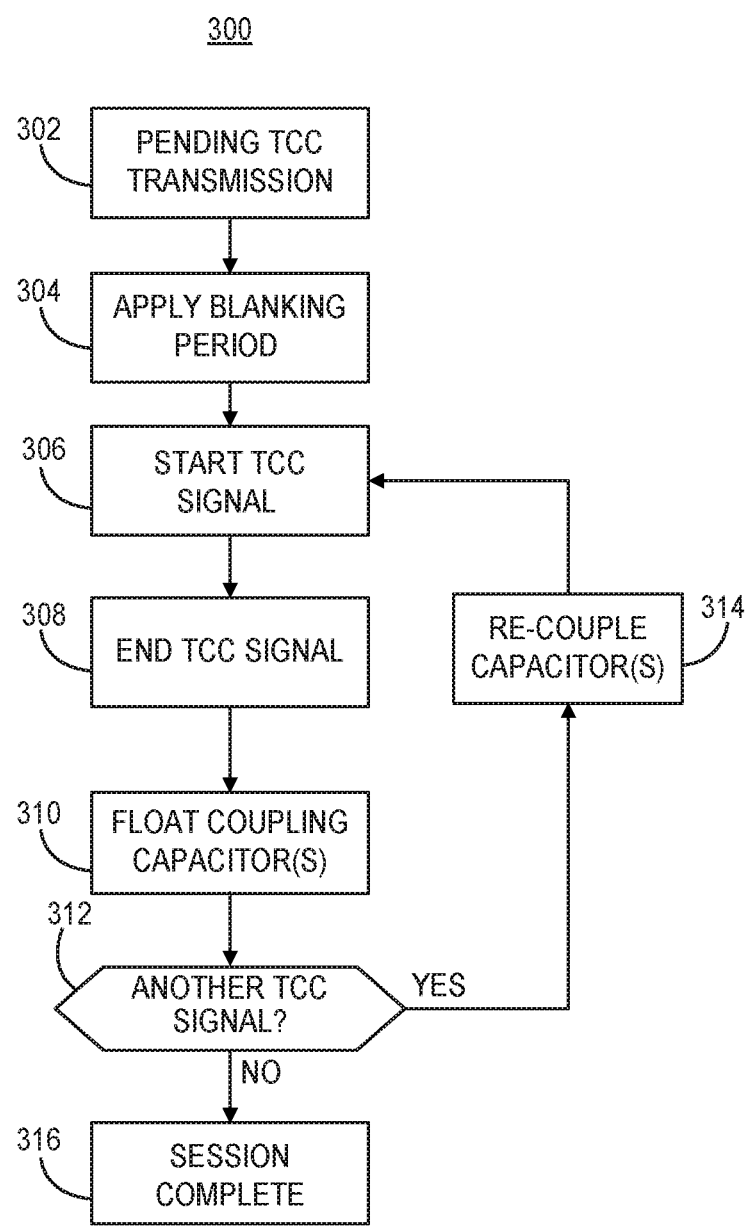
FIG. 8 is a flow chart of a method for transmitting TCC signals by an IMD according to one example.

FIG. 8 is a flow chart 300 of a method for transmitting TCC signals of a TCC session by an IMD according to one example. TCC transmission session includes a plurality of TCC signals that are transmitted. The process of flow chart 300, and other flow charts presented herein, may be performed by TCC transmitter 90 under the control of control circuit 80. In the description provided, the transmitting IMD may be ICD 14 or ICD 214, however pacemaker 100, pressure sensor 50 or another IMD may include TCC transmitter 90 configured to perform the transmission methods of FIG. 8 and other flow charts provided herein.

At block 302, the ICD control circuit 80 determines that a TCC signal transmission is pending. One or more TCC signals may be transmitted in a signal TCC transmission session, which may include one or more beacon signals and/or at least one data packet. Each TCC signal may transmitted as a carrier signal, which may be modulated to encode data using a selected modulation technique, for example using FSK, PSK. In the case of ICD 14 or ICD 214 including a cardiac event detector 85, control circuit 80 may control TCC transmitter 90 to initiate at least the first TCC signal of a transmission session during a blanking period at block 304. The first TCC signal may be a beacon signal transmitted to wake up a receiving device, e.g., pacemaker 100 or pressure sensor 50.

In other instances, however, the first TCC signal may occur outside of a blanking period. For example, controller 91 may control transmitter 90 to transmit the first TCC signal at block 306 as a ramp on signal that gradually increases the peak-to-peak amplitude of the carrier signal as described above to reduce low frequency signal artifact during a "cold start." AC coupling capacitor 96 is gradually charged to the DC operating voltage from a discharged state during the ramp on signal. One example technique of starting the TCC signal with a ramp on signal is generally disclosed in U.S. Pat. Application No. 62/591,813 (Peichel) referenced above and incorporated herein by reference in its entirety. If the first TCC signal is a ramp on signal, starting the first TCC signal during the blanking period applied at block 304 is optional.

At the start of a transmission session, the early cycles of the carrier frequency signal establish a DC voltage across the AC coupling capacitor 96. During this time, which may be 10 ms, 50 ms, 100 ms, or even up to 200 ms or more, a low frequency current may be injected into the conductive body tissue pathway via the TCC transmission electrode vector. The low frequency current is more likely to cause interference with the cardiac event detector 85 (or other electrophysiological sensing circuits of other implanted devices) than the relatively high frequency of TCC signal carrier frequency. By starting the first data packet of each transmission session during a blanking period applied to the sensing circuit 86 of the transmitting device, the DC voltage is established on the AC coupling capacitor 96 mostly or entirely during the blanking period when the sensing circuit 86 is blanked and relatively immune to the low frequency artifact.

The blanking period may be an automatic blanking period that the control circuit 80 applies to the cardiac event detector 85 following an intrinsic or paced cardiac event. A post-sense blanking period is set in response to an intrinsic cardiac event, e.g., an R-wave or P-wave, sensed by cardiac event detector 85. A post-pace or post-shock blanking period may be automatically applied to the cardiac event detector 85 upon delivery of a cardiac electrical stimulation pulse by therapy circuit 83. For example, a post-sense blanking period may be applied to a sense amplifier or other cardiac event detection circuitry in response to a cardiac event sensing threshold crossing. A post-pace or post-shock blanking period may be applied to prevent saturation of the sense amplifier(s) during delivery of a pacing pulse or cardioversion/defibrillation shock. An automatic post-sense or post-pace blanking period may be in the range of 50 to 200 ms, and may be 150 ms, for example. The low frequency artifact that may occur at the beginning of a TCC carrier signal transmission as AC coupling capacitor 96 is charged to a DC operating voltage is not detected as a cardiac event by cardiac event detector 85 during a blanking period. Furthermore, during the post-sense, post-pace or post-shock blanking period, myocardial tissue is in a state of physiological refractoriness such that any low frequency signal injected at the beginning of a TCC signal is highly unlikely to capture the myocardial tissue.

In some examples, the TCC transmission session is initiated at block 306 by starting transmission of the first data packet of the transmission session during an automatic blanking period that is applied to the cardiac event detector 85 by control circuit 80 based on the timing of sensed cardiac events and/or delivered electrical stimulation pulses. Control circuit 80 may be configured to identify a cardiac event, sensed or pace, apply a blanking period to the sensing circuit 86 in response to identifying the cardiac event, and control TCC transmitter 90 to start transmission of a the first TCC signal during the blanking period. In other examples, control circuit 80 may apply a communication blanking period to cardiac event detector 85 independent of the timing of cardiac electrical events, sensed or paced. In some cases, a communication blanking period may be applied during the cardiac cycle between sensed or paced events. The communication blanking period may be applied by control circuit 80 to the cardiac event detector 85 to enable TCC signal transmission to be initiated at block 306 at any time during the cardiac cycle, without waiting for an automatic post-sense or post-pace blanking period. A communication blanking period may be much shorter or longer than the automatic post-sense or post-pace blanking period. For example, a communication blanking period may be in the range of 10 ms to 200 ms and may depend on the programmed sensitivity of the cardiac event detector 85 and the duration of low frequency interference at the start of TCC signal transmission. The maximum duration of the communication blanking period may be limited based on the particular clinical application. For example, in the cardiac monitoring and therapy delivery IMD systems 10 and 200 disclosed herein (FIG. 1 and FIG. 2, respectively), the maximum time that cardiac event detector 85 is blinded to detecting cardiac events may be 200 ms or less. In non-cardiac applications, e.g., monitoring muscle or nerve signals, longer or shorter communication blanking periods may be required.

At block 306, the transmission of the first TCC signal begins during the blanking period. Controller 91 may control drive signal circuit 92 and/or polarity switching circuit 94 to encode data, e.g., using FSK, BPSK, or other modulation schemes. The controller 91 may modulate the TCC signals during the transmission session according to a modulation scheme that includes FSK modulation of beacon signals and BPSK modulation of data packets as generally disclosed in U.S. Pat. Application No. 62/591,810 (Reinke), incorporated herein by reference in its entirety. At block 308 transmission of the TCC signal is complete. Controller 91 controls the voltage holding circuit 98 at block 310 to hold the DC voltage on the AC coupling capacitor 96 in accordance with the techniques of this disclosure. In one example, voltage holding circuit 98 may be controlled to disconnect the AC coupling capacitor 96 by opening switches, e.g., switches 320a and 322a and/or 320b and 322b (FIG. 7), to float the AC coupling capacitor 96 at the DC voltage established during the TCC signal just transmitted. However, other techniques for holding the AC coupling capacitor 96 at or near the DC voltage may be used as described elsewhere herein.

If the pending TCC transmission includes another TCC signal for transmission, as determined at block 312, voltage holding circuit 98 is controlled to close switches 320a, 320b, 322a and 322b at block 314 to re-connect the AC coupling capacitor 96 between the polarity switching circuit 94 and the selected transmission electrode vector 99. Transmission of the next TCC signal begins at block 306 with reduced or minimized low frequency artifact at the start of the next TCC signal transmission since the previously-established DC voltage has been held on the AC coupling capacitor 96. As such, the start of the next TCC signal transmission, which may be a subsequent beacon signal or data packet, may occur outside a blanking period applied to the cardiac event detector 85. Transmission of the next TCC signal is not necessarily tied to the timing of blanking periods during the cardiac cycle or limited to being started once per cardiac cycle during automatic blanking periods. If used, communication blanking periods can be applied less frequently to the cardiac event detector 85 when the AC coupling capacitor voltage is held by the voltage holding circuit 98 between TCC signal transmissions, reducing how often the cardiac event detector 85 is "blinded" during a TCC transmission session. It is recognized, however, that when TCC transmitter 90 and therapy circuit 83 share an electrode vector and/or pulse generation circuitry of signal generator 84, TCC signal transmission may not occur simultaneously with a cardiac electrical stimulation therapy pulse. TCC signal transmission is generally performed at distinctly separate times from therapy delivery since the TCC transmission electrode vector may provide an inappropriate return path for stimulation energy being delivered by a therapy delivery electrode vector.

By holding the AC coupling capacitor 96 at or near the DC voltage between consecutive TCC signal transmissions, the low frequency artifact is reduced at the start of each TCC signal, reducing the likelihood of false detection of a cardiac event by cardiac event detector 85. This process of disconnecting the AC coupling capacitor 96 by voltage holding circuit 98 after each TCC signal transmission to float the AC coupling capacitor 96 at the DC voltage established (or maintained) during the immediately preceding TCC signal transmission may continue until all TCC signals scheduled for transmission have been transmitted during the session. In some examples, controller 91 may determine that another beacon signal needs to be transmitted at block 312 if a response to a preceding beacon signal was not received from the intended receiving device. In other instances, one or more data packets may be transmitted after an acknowledged beacon signal during a single transmission session. Once all data packets have been transmitted, as determined at block 312, the transmission session is complete at block 316.

In some examples, the AC coupling capacitor 96 may be actively discharged at block 316 through a resistive pathway or allowed to passively discharge through leakage current pathways until the next TCC transmission session. The peak-to-peak amplitude of the carrier signal of the last data packet may be stepped down in a ramp off signal in some examples so that the DC voltage across the AC coupling capacitor 96 is in a known state at the start of the next TCC signal transmission. AC coupling capacitor voltage holding techniques disclosed herein may be implemented in a system that transmits a ramp on signal as the first TCC signal during a transmission session and/or provides a ramp off signal at the end of the transmission session to provide controlled rates of charging and discharging the AC coupling capacitor 96 as generally disclosed in U.S. Pat. Application No. 62/591,813 (Peichel), incorporated herein by reference in its entirety.

If transmission sessions occur relatively infrequently, each transmission session may begin during a blanking period as described above to allow the DC voltage to be developed across the AC coupling capacitor 96 during a time that the cardiac event detector 85 is blanked and the myocardial tissue may be in physiological refractory. In other examples, however, the AC coupling capacitor 96 may be floated at the established DC voltage after the last data packet of a transmission session until the start of the next TCC transmission session. If TCC transmission sessions are expected to occur relatively frequently, or at least the next TCC transmission is expected to occur soon after the current TCC transmission session, the voltage holding circuit 98 may be controlled to disconnect the AC coupling capacitor 96 to float the AC coupling capacitor 96 at the DC voltage established during the last data packet until the next TCC transmission session is started. In this case, the next TCC transmission may be started outside a blanking period. The voltage holding circuit 98 may be controlled to hold the AC coupling capacitor 96 at an established DC voltage for up to ten minutes, up to five minutes, up to two minutes, or up to one minute between TCC transmission sessions. The time duration that the voltage holding circuit 98 is capable of holding the AC coupling capacitor 96 at an established DC voltage may vary between systems due to the extent of leakage currents in the circuitry of the transmitter 90.

While not shown explicitly in FIG. 8, it is to be understood that the transmitting device, e.g., ICD 14 or 214, may toggle between transmitting and receiving during a transmission session when the receiving device is configured for bi-directional communication with the transmitting device. In this case, after transmitting each TCC signal, before starting the next TCC signal transmission, the transmitting device may enable TCC receiver 87 to detect a voltage signal developed on a receiving electrode vector selected from the available electrodes, e.g., 24, 26, 28 and 30 and housing 15 (FIG. 5). In some examples, the receiving electrode vector is the same as the transmitting electrode vector, e.g., electrode 24 and housing 15 as shown in example of FIG. 6. As such, during the time period that the voltage holding circuit 98 is floating the AC coupling capacitor 96 at block 310, the TCC receiver 87 is enabled for receiving TCC signals.

Figure 9:
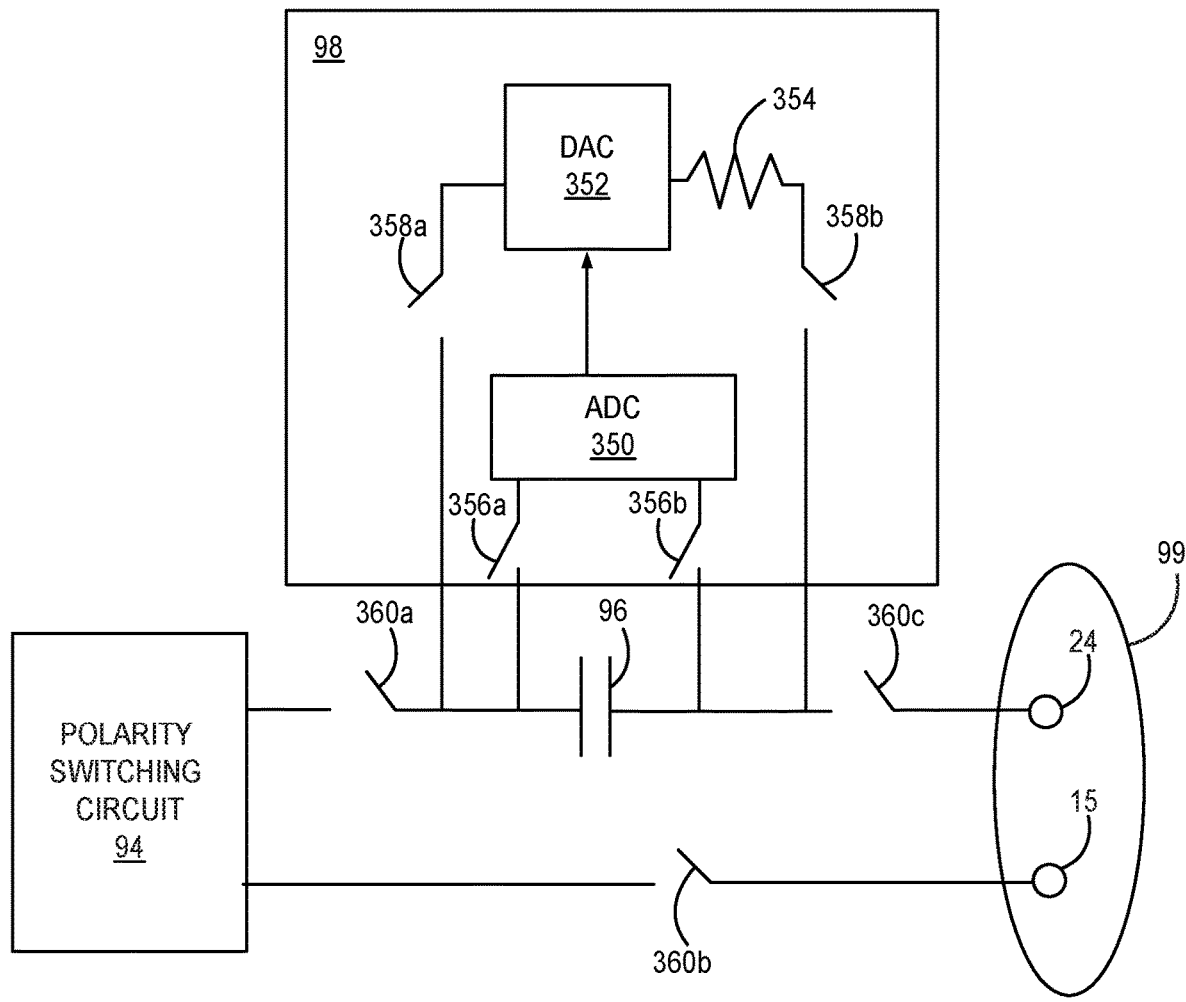
FIG. 9 is a conceptual diagram of circuitry included in a TCC transmitter including a voltage holding circuit according to another example.

FIG. 9 is a conceptual diagram of circuitry included in TCC transmitter 90 including voltage holding circuit 98, according to another example. In this example, the voltage holding circuit 98 actively holds the DC voltage developed on AC coupling capacitor 96 between TCC signal transmissions. Voltage holding circuit 98 may include an analog-to-digital converter (ADC) 350, a digital-to-analog converter (DAC) 352, a resistor 354 and multiple switches 356a, 356b, 358a and 358b. A combination of switches 360a, 360b and 360c are controlled by controller 91 to open and uncouple AC coupling capacitor 96 from the transmission electrode vector 99 and polarity switching circuit 94 after transmission of a TCC signal is complete.

Controller 92 controls voltage holding circuit 98 to connect AC coupling capacitor 96 to ADC 350 at the end of the TCC signal transmission by closing switches 356a and 356b. Switches 360a, 360b and 360c may be opened unless ADC 350 has a high input impedance in which case opening switches 360a-c may be optional. ADC 350 detects the DC voltage across AC coupling capacitor 96. ADC 350 passes the digital value of the DC voltage to DAC 352. Controller 91 controls switches 358a and 358b to couple AC coupling capacitor 96 to DAC 352. Depending on the input impedance of ADC 350, switches 356a and 356b may be opened to uncouple ADC 350 from AC coupling capacitor 96. DAC 352 applies a differential holding voltage (based on the signal from ADC 350) across AC coupling capacitor 96 between TCC signal transmissions. In this example, resistor 354 is not required since AC coupling capacitor 96 and DAC 352 are disconnected from the polarity switching circuit 94 and transmitting electrode vector 99.

In other examples, at least some of switches 356a, 356b, 358a, 358b, 360a, 360b, and 360c are optional. AC coupling capacitor 96 may remain coupled to one or both of transmitting electrode vector 99 and polarity switching circuit 94 between TCC signal transmissions. ADC 350 may sample the voltage across AC coupling capacitor 96 at the end of a TCC signal transmission and pass the digital voltage signal to DAC 352. DAC 352 may apply the differential holding voltage to AC coupling capacitor 96 through resistor 354, which may be a high value weak resistor. Resistor 354 limits the rate of any voltage change across AC coupling capacitor 96 to limit current artifact injected into the tissue pathway via electrode vector 99 between TCC signal transmissions. In still other examples, voltage holding circuit 98 does not require ADC 350. DAC 352 may include a comparator for determining the voltage across AC coupling capacitor 96 and apply the determined voltage across AC coupling capacitor, through resistor 354 if AC coupling capacitor 96 is not uncoupled from transmitting electrode vector 99.

At the start of the next TCC signal transmission, the switches 356a, 356b, 358a, 358b, 360a, 360b, and 360c are controlled to disconnect AC coupling capacitor 96 from voltage holding circuit 98 and re-couple AC coupling capacitor 96 to transmission electrode vector 99 and polarity switching circuit 94. Since AC coupling capacitor 96 has been actively held at the DC operating voltage, TCC signal transmission may begin without introducing low frequency current artifact of any significance and may therefore begin outside a blanking period and without a ramp on signal.

FIG. 9 represents one example of voltage holding circuit 98 configured to digitally control the voltage across AC coupling capacitor 96 using ADC 350 and DAC 352 during time periods between TCC signal transmissions. It is contemplated that other digital or analog circuits or combinations thereof may be conceived for holding AC coupling capacitor 96 at a DC operating voltage between TCC signal transmissions. For example, voltage holding circuit 98 may include a low leakage storage capacitor between switches 358a and 358b substituted for DAC 352. Controller 91 may control switches 358a and 358b to couple AC coupling capacitor 96 across the storage capacitor between TCC signal transmissions. The voltage established on AC coupling capacitor 96 during a TCC signal transmission may be stored on the storage capacitor when transmitter 90 is not transmitting a TCC signal. In this case ADC 350 may not be needed for sampling the voltage across AC coupling capacitor 96. Voltage holding circuit 98 may include an amplifier circuit to drive the stored voltage from the storage capacitor to the AC coupling capacitor 96 so that the AC coupling capacitor 96 is charged back up to its DC operating voltage prior to the next TCC signal. The high value resistor 354 may be used to limit the rate of recharge.

Figure 10:
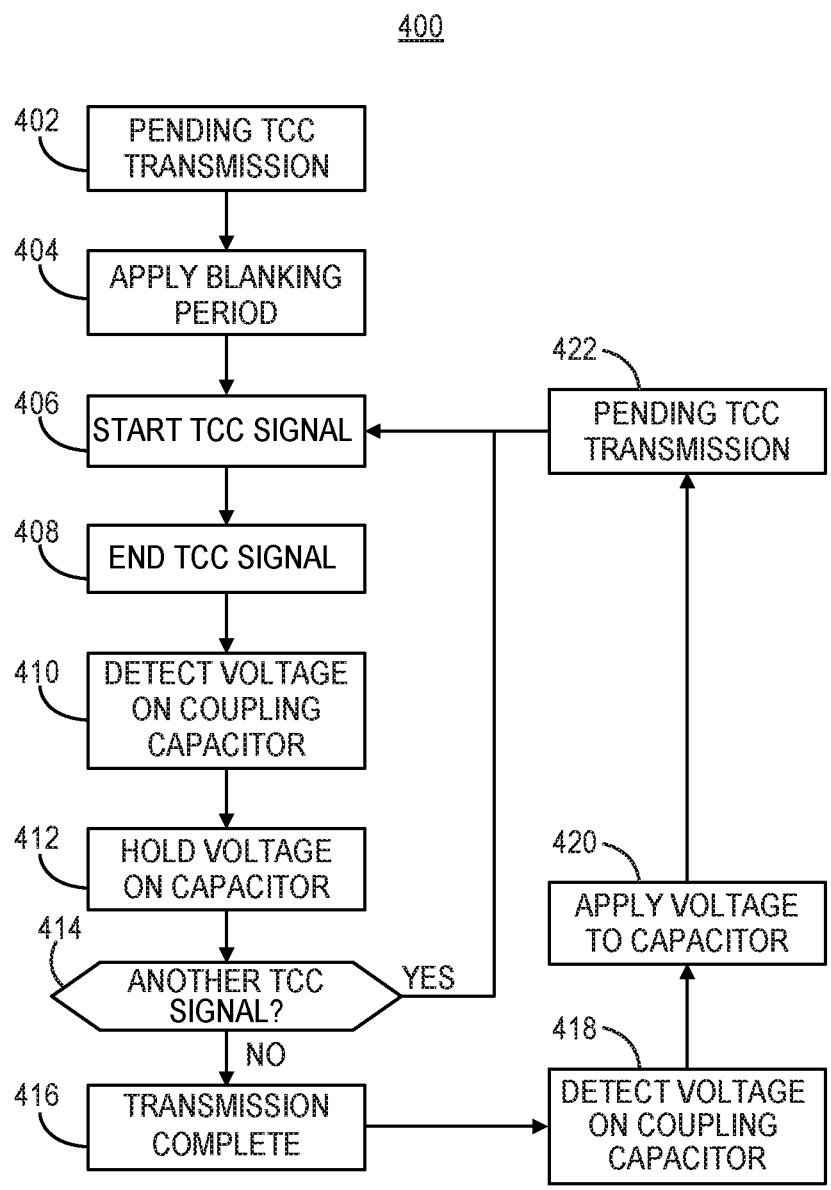
FIG. 10 is a flow chart of a method for transmitting TCC signals according to another example.

FIG. 10 is a flow chart 400 of a method for transmitting TCC signals according to another example using the TCC transmitter 90 and voltage holding circuit 98 shown in FIG. 9. At block 402, control circuit 80 determines that a TCC transmission is pending. At block 404, control circuit 80 may wait for a post-sense or post-pace blanking period to be applied to the cardiac event detector 85. In other examples, control circuit 80 may apply a communication blanking period as described above. Control circuit 80 may the TCC transmitter 90 to start transmitting the first TCC signal of the transmission session during a blanking period at block 406. In other examples, controller 91 may control transmitter 90 to transmit the first TCC signal at block 406 as a ramp on signal that gradually increases the peak-to-peak amplitude of the carrier signal as described above to reduce low frequency signal artifact during a "cold start." AC coupling capacitor 96 is gradually charged to the DC operating voltage from a discharged state during the ramp on signal, as described generally in referenced U.S. Pat. Application No. 62/591,813 (Peichel). If the first TCC signal is a ramp on signal, starting the first TCC signal during the blanking period applied at block 404 is optional.

During or immediately after completing transmission of the first TCC signal (block 408), controller 91 closes switches 356a and 356b and enables ADC 350 (FIG. 9) to detect the voltage established across the AC coupling capacitor 96 at block 410. A digital signal indicating the established voltage is passed to DAC 352. At block 412, the DAC actively holds the AC coupling capacitor 96 by applying the detected voltage across AC coupling capacitor 96. If AC coupling capacitor is not uncoupled from the transmission electrode vector, the DC voltage may be applied to AC coupling capacitor 96 by DAC 352 through a high, weak resistor 354 to avoid artifact.

If the next TCC signal is ready to be transmitted, as determined at block 414, transmission is started at block 406 after decoupling AC coupling capacitor 96 from voltage holding circuit 98 (e.g., by opening switches 356a, 356b, 358a, and 358b). If switches 360a-c are used to uncouple AC coupling capacitor from transmitting electrode vector 99 and polarity switching circuit 94, controller 91 closes switches 360a-c. TCC transmitter 90 may not wait for a blanking period to be applied to the sensing circuit 86 before transmitting the next TCC signal since the AC coupling capacitor 96 has been held at or near the DC operating voltage. The TCC signal transmission may immediately inject current at or near the relatively high carrier frequency, e.g., 100 kHZ, which is not expected to interfere with the cardiac event detector 85 or capture the myocardium or other excitable tissue.

After each TCC signal transmission, the voltage on AC coupling capacitor 96 may be sampled at block 410 by ADC 350, and the detected voltage is applied by DAC 352 (block 412) from the end of one TCC signal transmission until the start of the next TCC signal transmission. Sampling the DC voltage across AC coupling capacitor 96 after each TCC signal may ensure any DC voltage shifts that may occur are tracked. In other examples, however, the DC voltage may be sampled by ADC 350 less frequently than every TCC signal. For example, the voltage may be sampled after only the first TCC signal of a transmission session or after every nth TCC signal during a transmission session A previously sampled voltage is applied by DAC 352 until a new digital signal from ADC 350 is received, at which time the applied voltage may be adjusted accordingly.

If all TCC signals to be transmitted during the transmission session have been transmitted, as determined at block 414, the current TCC transmission session is complete at block 416. At block 418, the voltage holding circuit 98 may be controlled to detect the voltage on the AC coupling capacitor 96 at or near the end of the last TCC signal of the completed transmission session. The voltage holding circuit 98 may hold the AC coupling capacitor 96 at or near the DC voltage determined by ADC 350 using DAC 352 (and optionally resistor 354) at block 420. The AC coupling capacitor 96 is held at or near the DC operating voltage from the end of one TCC transmission session until the start of the next transmission session. Control circuit 80 may determine that the next TCC transmission is pending at block 422. Transmission of the first TCC signal of the next TCC transmission session may be started at block 406, without waiting for an automatic blanking period or applying a communication blanking period. By holding the DC voltage on the AC coupling capacitor 96 between transmission sessions, low frequency artifact at the onset of the first packet of the next transmission session is eliminated or reduced. Application of a blanking period (at block 404) at the start of the next transmission session is optional.

Alternatively, the voltage on the AC coupling capacitor 96 may be sampled by ADC 350 at the end of a completed transmission session (block 418), and, instead of actively holding the AC coupling capacitor 96 at the sampled voltage until the next transmission session, AC coupling capacitor 96 may be allowed to discharge. The sampled voltage may be applied to the AC coupling capacitor 96 at block 420 to charge the AC coupling capacitor 96 back up to the detected voltage level when the next TCC transmission session is pending (block 422). In this way, power source 98 may be conserved by not actively holding the AC coupling capacitor 96 at the detected voltage for a prolonged time period.

Figure 11:
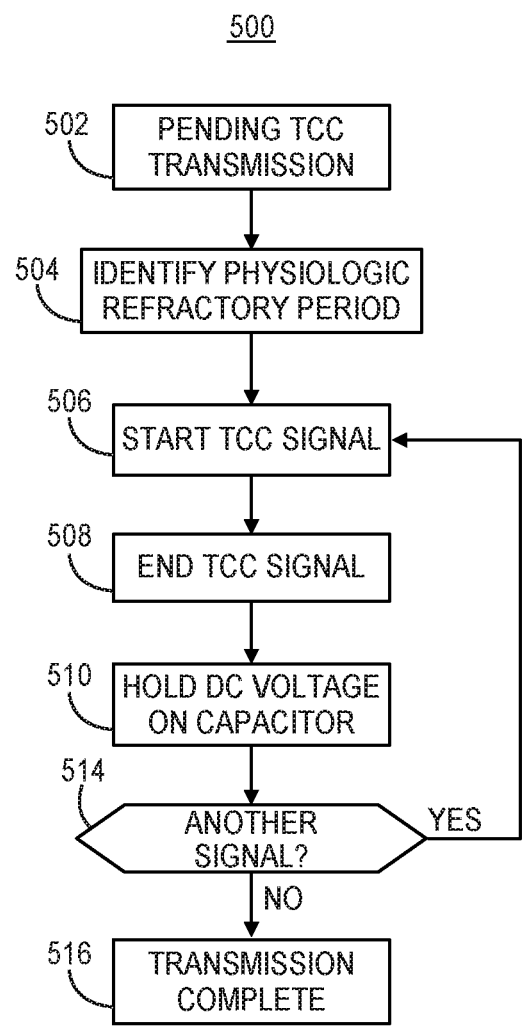
FIG. 11 is a flow chart of a method for TCC signal transmission according to another example.

FIG. 11 is a flow chart 500 of a method for TCC signal transmission according to another example. Upon scheduling a pending TCC transmission session at block 502, control circuit 80 may identify a physiological refractory period at block 504. Control circuit 80 may be configured to identify the physiological refractory period based on a sensed event signal from cardiac event detector 173. The physiological refractory period of the myocardium may follow an intrinsic sensed event. At other times, control circuit 80 may identify the physiological refractory period based on an evoked response expected after a cardiac electrical stimulation pulse, e.g., a pacing pulse. The pacing pulse may be delivered by the transmitting device, e.g., ICD 14 or ICD 214, or a different, co-implanted device, e.g., pacemaker 100. The time of the physiological refractory period may be identified at block 504 indirectly based on detecting a sensed or paced cardiac event.

At block 506, the control circuit 80 controls TCC transmitter 90 to start transmitting the first TCC signal of the transmission session during the physiologic refractory period. For example, transmission of the first TCC signal may be started within a predetermined time interval after a sensed or paced cardiac event corresponding to the expected refractory period of the myocardium. After transmission of the first TCC signal has ended, at block 508, the voltage holding circuit 98 of TCC transmitter 90 is controlled to hold the DC voltage developed on the AC coupling capacitor 96 at block 510. The DC voltage may be held on the AC coupling capacitor 96 using any of the techniques disclosed above. If the transmission session includes more than one TCC signal, e.g., multiple packets of data, as determined at block 514, additional TCC signals are transmitted by repeating blocks 506 through 510 until all TCC signals during the transmission session are transmitted, and the transmission session is complete at block 516.

In some examples, the DC voltage is held on the AC coupling capacitor 96 by the voltage holding circuit 98 between transmission sessions. In other examples, each transmission session is started during a physiologic refractory period and the DC voltage is held on the AC coupling capacitor 96 between consecutively transmitted packets during the transmission session. Once the first TCC signal of a transmission session is started during the physiological refractory period, subsequent TCC signals of the transmission session may be started outside the physiological refractory period when AC coupling capacitor 96 is held at or near the DC voltage between consecutively transmitted TCC signal packets.

Figure 12:
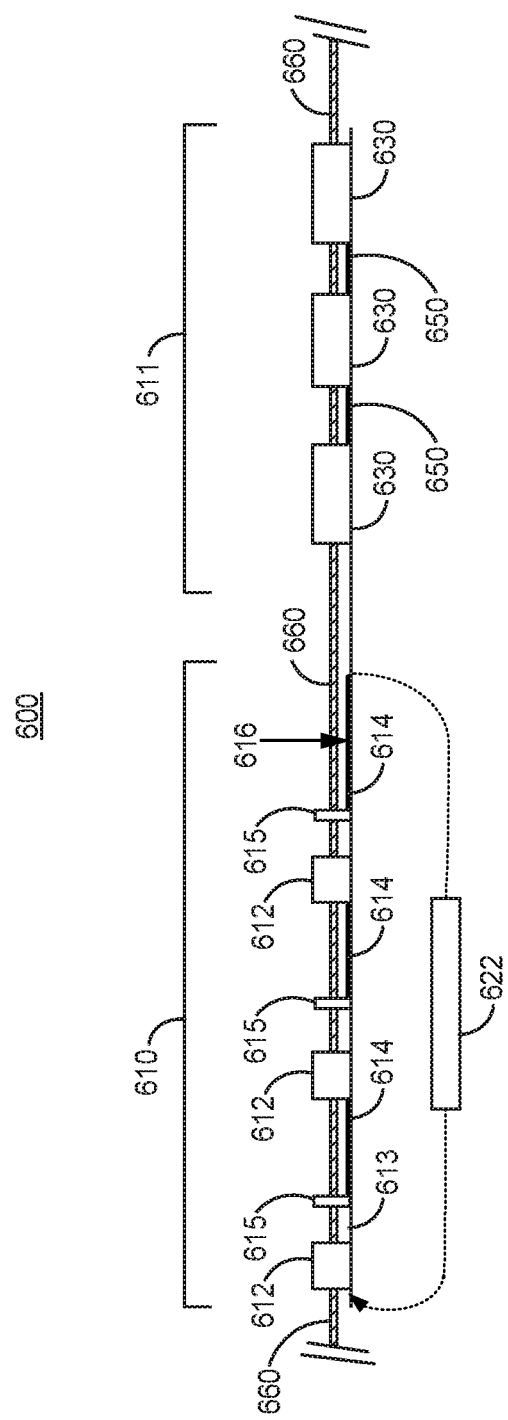
FIG. 12 is a conceptual diagram of one example of a TCC transmission session performed by a transmitting device of an IMD system.

FIG. 12 is a conceptual diagram of one example of a TCC transmission session 600 performed by a transmitting device of an IMD system, such as ICD 14 of system 10 or ICD 214 of system 200, shown in FIG. 1 and FIG. 2 respectively. The control circuit 80 (FIG. 5) controls transmitter 90 to start transmission session 600 by signaling controller 91 to transition the transmitter 90 from a sleep mode (reduced power with drive signal circuit 92 and polarity switching circuit 94 inactive) to a wakeup mode 610. Controller 91 controls drive signal circuit 92 and polarity switching circuit 94 to generate a beacon signal 612 to start the TCC transmission session 600.

In FIG. 12, voltage holding intervals 660 are indicated between transmitted TCC signals throughout the TCC transmission session 600 and may precede the first beacon signal 612. The voltage holding circuit 98 may be enabled to hold the AC coupling capacitor 96 at or near a DC voltage established on the AC coupling capacitor 96 during a preceding transmission session as indicated by voltage holding interval 660, preceding the first beacon signal 612. In this case, the first beacon signal 612 may be transmitted without requiring synchronization with a blanking period. At other times, however, the first beacon signal 612 may not be preceded by a voltage holding interval 660, particularly if a relatively long time has elapsed since a preceding transmission session (e.g., more than 10 minutes). In this case, the AC coupling capacitor 96 is charged to a DC operating voltage during the first beacon signal 612. The first beacon signal 612 may be synchronized to a blanking period applied to cardiac event detector 85 as described above. In other examples, in the absence of a voltage holding interval 660 preceding the first beacon signal 612, the first transmitted signal of transmission session 600 may be a ramp on signal during which the AC coupling capacitor 96 is charged gradually over step up intervals and step increments of the carrier signal amplitude as disclosed in the above-incorporated U.S. Pat. Application No. 62/591,813 (Peichel, C00010640.USP1).

The controller 91 may control the drive signal circuit 92 and/or polarity switching circuit 94 to wait for a post-beacon interval 613 after beacon signal 612 before transmitting an OPEN command 615. The post-beacon interval 613 is provided to allow time for the receiving device to detect the beacon signal 612 and power up the TCC signal detector 175 to enable searching for the OPEN command 615. The beacon signal 612 may be 50 ms to 1 second in duration and is 80 to 120 ms in some examples. The beacon signal 612 may be followed by a post-beacon interval 613 that is 100 ms to 200 ms in duration. The voltage holding circuit 98 may hold the AC coupling capacitor 96 at or near the DC voltage sampled by ADC 350 at the end of the first beacon signal 612 during the post-beacon interval 613 or float the AC coupling capacitor 96 at or near its DC operation voltage during post-beacon interval 613.

Relatively short beacon signals 612, e.g., 8 to 120 ms, may be repeated at multiple times during the cardiac cycle to promote transmission at a time that the receiving electrode vector is parallel to the tissue conductance pathway of the injected current. In the example shown, each beacon signal 612 is followed by an OPEN command 615. In other examples, the beacon signal 612 may be transmitted repeatedly, e.g., two or more times during a cardiac cycle, separated by post-beacon intervals 613 and a single OPEN command 615 is transmitted after all of the multiple short beacon signals 612 to increase the likelihood of the beacon signal being detected by the receiving device in advance of the OPEN command 615. The voltage holding circuit 98 may be controlled by controller 91 to sample the voltage across the AC coupling capacitor 96 after each beacon signal 612 and/or after each OPEN command 615 to apply a voltage holding interval 660 until the next TCC signal transmission. In other examples, voltage holding circuit 98 floats the AC coupling capacitor 96 after each beacon signal 612 and/or OPEN command 615 during wake-up mode 610.

In some examples, the transmitting device control circuit 80 may enable the TCC receiver 87 to search for an acknowledgement signal from the receiving device during an acknowledgement receiving period 614 following each OPEN command 615 or each beacon signal 612. Receiving period 614 may have a maximum duration for waiting for an acknowledgment signal. If an acknowledgement signal is not detected by the transmitting device by the expiration of the receiving period 614, the transmitting device may transmit another beacon signal 612. The beacon signal 612 may be repeatedly delivered, followed by post-beacon interval 613, OPEN commands 615 and acknowledgment signal receiving period 614 until an acknowledgment detect signal 616 is generated by the TCC receiver 87.

In some cases, if a predetermined number of beacon signals 612 are delivered and the acknowledgment signal is not received, the controller 91 may control transmitter 90 to wait for a beacon control interval 622, as indicated by the curved dashed arrow, before sending another beacon signal 612. The voltage holding circuit 98 may be enabled to hold the AC coupling capacitor 96 at or near the DC operating voltage during beacon control interval 622. As such, during the wake-up mode 610 of transmitter 90, voltage holding circuit 98 may be controlled by controller 91 to apply a voltage holding interval 660 during any or all of the post-beacon interval(s) 613, acknowledgment receiving period(s) 614, and beacon control interval(s) 622.

Upon detection of the acknowledgement signal transmitted from the receiving device during the receiving period 614, an acknowledgement detect signal 616 may be generated by the TCC receiver 87 and passed to control circuit 80 of the transmitting device. Control circuit 80 switches TCC transmitter 90 from the wakeup mode 610 to the data transmission mode 611 to begin transmitting data packets 630. The voltage holding circuit 98 may hold the AC coupling capacitor 96 at or near the DC voltage sampled by ADC 350 at the end of the last transmitted signal, e.g., at the end of the last OPEN command 615, during a voltage holding interval 660 until the first data packet 630. In other examples, the voltage holding circuit 98 floats the AC coupling capacitor 96 at or near its DC operating voltage from the end of the last OPEN command 615 until the start of the first data packet 630.

During the transmission mode 611, one or more datagrams or data packets 630 may be transmitted using a modulated carrier signal, e.g., an FSK or PSK modulated signal. Each data packet 630 may include one or more bytes for transmitting an encoded command or data. In one example, controller 91 may be configured to control the drive signal circuit 92 and polarity switching circuit 94 to generate BPSK modulated signals during the data transmission mode 611, e.g., by producing 180-degree phase shifts in the carrier signal to encode digital signals in the modulated carrier signal. Methods for transmitting a BPSK signal by TCC transmitter 90 disclosed in the above-incorporated U.S. patent application Ser. No. 16/202,418 (Roberts) and U.S. Patent Application No. 62/591,810 (Reinke) may be used in conjunction with the various examples of the voltage holding circuit 98 and voltage holding intervals 660 disclosed herein.

Packets 630 may be separated by receiving windows 650 during which TCC receiver 87 may be enabled to detect signals transmitted by the receiving device, such as a confirmation signal or other data requested by the transmitting device. Voltage holding circuit 98 may be enabled to float the AC coupling capacitor 96 during each receiving window 650 or hold the AC coupling capacitor at or near the DC operating voltage sampled at the end of each data packet 630 by ADC 350 for the duration of each receiving window 650. The TCC transmission session 600 is terminated following the last packet 630, and transmitter 90 may return to a low power, sleep state. Controller 91 may control voltage holding circuit to hold the AC coupling capacitor 96 at or near a DC voltage sampled by ADC 350 at the end of the last packet 630 during a voltage holding interval 660 that extends from the end of the last packet 630 until the first TCC signal of the next transmission session or until a particular time period expires, e.g., 10 minutes. Alternatively, voltage holding circuit 98 may be configured to float the AC coupling capacitor 96 at or near its established DC operating voltage from the end of the last data packet 630 until the first TCC signal of the next transmission session or until a particular time period expires, e.g., 10 minutes. In still other examples, the voltage across the AC coupling capacitor 96 may be sampled at the end of TCC transmission session 600, and voltage holding circuit may be configured to recharge the AC coupling capacitor 96 to the sampled voltage prior to the next TCC transmission session as described above.

In the example of FIG. 12, voltage holding intervals 660 are shown to extend before and after each transmitted signal, e.g., before and after each beacon signal 612, OPEN command 615, and data packet 630. Controller 91 may control voltage holding circuit 98 to sample the voltage across the AC coupling capacitor 96 at the end of each transmitted signal (or less frequently) and apply the voltage to the AC coupling capacitor 96 until the start of the next TCC signal. In other examples, the voltage holding circuit 98 is configured to uncouple the AC coupling capacitor 96 to float the AC coupling capacitor 96 at or near its DC operating voltage from the end of one TCC signal until the start of the next TCC signal. While a voltage holding interval 660 is shown to extend between each consecutive pair of transmitted TCC signals in FIG. 12 as well as before the first beacon signal 612 and after the last data packet 630, it is to be understood that the voltage holding circuit 98 may be enabled between some TCC signal transmissions and may not be enabled between other TCC signal transmissions. In some cases, the time interval between TCC signals is relatively short and/or the leakage currents very low such that discharging of the AC coupling capacitor 96 between TCC signals is insignificant. For example, voltage holding interval 660 during post beacon interval 613 may not be needed if leakage current from AC coupling capacitor 96 is low and post-beacon interval 613 is very short. Voltage holding intervals 660 may be optional during post-beacon intervals 613, during acknowledgement receiving periods 614, during beacon control intervals 622 and/or after the last TCC signal (e.g., the last OPEN command 615) during wake-up mode 610 until the first data packet 630 depending on how long the time between two successive TCC signals is and the inherent leakage current in transmitter 90. Voltage holding intervals 660 may be applied during one or more time periods between TCC signals during a transmission session 600 and/or between TCC transmission sessions and is not necessarily required between all TCC signals.

Furthermore, while each example of voltage holding techniques disclosed herein may be implemented as the only voltage holding technique, different techniques may be combined within transmitter 90. For instance, AC coupling capacitor 96 may be floated at or near its DC operating voltage between some TCC signal transmissions and actively held at or near its DC operation voltage by a DAC between other TCC signal transmissions or between TCC communication sessions. While specific examples of voltage holding circuits are described herein, it is contemplated that a variety of voltage holding circuits may be included in transmitter 90 that include any combination of components, such as switches, resistors, capacitors, DACs, ADCs, comparators, or other components, configured to hold the AC coupling capacitor 96 at a DC voltage previously established on AC coupling capacitor 96, e.g., during a preceding TCC signal transmission.

Thus, a method and apparatus for transmitting TCC signals by device, such as an IMD, have been presented in the foregoing description with reference to specific embodiments. It is appreciated that various modifications to the referenced embodiments, including combining various aspects of the TCC signal transmission methods in different combinations than the specific combinations described here, may be made without departing from the scope of the disclosure and the following claims.

What is claimed is:

1. A device comprising:
    a housing; and
    a tissue conduction communication (TCC) transmitter enclosed by the housing and configured to generate a plurality of TCC signals, each of the plurality of TCC signals comprising a plurality of cycles of a carrier frequency signal, the TCC transmitter comprising:
        a coupling capacitor for coupling the generated TCC signals to a transmitting electrode vector to transmit the plurality of TCC signals via a conductive tissue pathway; and
        a voltage holding circuit configured to hold the coupling capacitor at a direct current (DC) voltage for a time interval between two consecutively transmitted TCC signals of the plurality of TCC signals.

2. The device of claim 1, wherein:
    the voltage holding circuit comprises at least one switch connecting the coupling capacitor to the transmitting electrode vector;
    the TCC transmitter comprises a controller configured to control the voltage holding circuit to hold the coupling capacitor at the DC voltage by:
        opening the at least one switch after a first of the two consecutively transmitted TCC signals, and
        closing the at least one switch at a start of a second of the two consecutively transmitted TCC signals.

3. The device of claim 2, wherein:
    the voltage holding circuit comprises at least two switches, a first switch connecting the coupling capacitor to a source of the TCC signal and a second switch connecting the coupling capacitor to the transmitting electrode vector;
    the TCC transmitter comprises a controller configured to control the voltage holding circuit to hold the coupling capacitor at the DC voltage by:
        opening the first and second switch after a first of the two consecutively transmitted TCC signals to float the coupling capacitor, and
        closing the first and second switch at a start of a second of the two consecutively transmitted TCC signals.

4. The device of claim 1, wherein the voltage holding circuit is further configured to:
    determine the DC voltage by detecting a voltage across the coupling capacitor; and
    apply the determined DC voltage across the coupling capacitor for the time interval between the two consecutively transmitted TCC signals.

5. The device of claim 4, wherein the voltage holding circuit comprises:
    an analog-to-digital converter configured to determine the DC voltage; and
    a digital-to-analog converter to receive the DC voltage from the analog-to-digital converter and apply the DC voltage across the coupling capacitor.

6. The device of claim 5, wherein the voltage holding circuit further comprises a resistor coupled to the digital-to-analog converter and the digital-to-analog converter applies the DC voltage through the resistor.

7. The device of claim 1, further comprising:
    a sensing circuit configured to receive a cardiac electrical signal from a patient's heart; and
    a control circuit configured to:
        apply a blanking period to the sensing circuit; and
        control the TCC transmitter to start transmitting at least a first one of the plurality of TCC signals during the blanking period.

8. The device of claim 7, wherein:
    the voltage holding circuit is configured to hold the coupling capacitor at the DC voltage for the time interval by holding the coupling capacitor at the DC voltage after a last TCC signal of a first transmission session until a first TCC signal of a second transmission session; and the control circuit is configured to control the TCC transmitter to start transmitting the first TCC signal of the second transmission session outside a second blanking period applied to the sensing circuit.

9. The device of claim 1, wherein the voltage holding circuit is configured to hold the coupling capacitor at the DC voltage for the time interval by holding the coupling capacitor at the DC voltage after a last TCC signal of a first transmission session until a first TCC signal of a second transmission session.

10. The device of claim 1, further comprising a control circuit configured to:
identify a physiological refractory period associated with one of an intrinsic or evoked cardiac event; and
control the TCC transmitter to start transmitting a first one of the plurality of TCC signals during the physiological refractory period.

11. The device of claim 1, wherein the voltage holding circuit is configured to hold the coupling capacitor within five percent (5%) of the DC voltage.

12. The device of claim 1, wherein:
the TCC transmitter includes a drive signal source and a polarity switching circuit configured to generate the plurality of TCC signals by generating the carrier frequency signal and modulating the carrier frequency signal, wherein the carrier frequency signal charges the coupling capacitor to the DC voltage during a first one of the plurality of TCC signals; and
the voltage holding circuit is configured to hold the coupling capacitor at the DC voltage by:
disconnecting the coupling capacitor between the polarity switching circuit and the electrode vector during a voltage holding interval between each of the plurality of TCC signals; and
during each of the voltage holding intervals, hold the coupling capacitor at a DC voltage established on the coupling capacitor during an immediately preceding one of the plurality of TCC signals.

13. A method comprising:
generating a plurality of tissue conduction communication (TCC) signals, each of the plurality of TCC signals comprising a plurality of cycles of a carrier frequency signal;
coupling the plurality of generated TCC signals to a transmitting electrode vector via a coupling capacitor to transmit the plurality of TCC signals via a conductive tissue pathway; and
holding the coupling capacitor at a direct current (DC) voltage for a time interval between two consecutively transmitted TCC signals of the plurality of TCC signals.

14. The method of claim 13, wherein holding the coupling capacitor at the DC voltage comprises:
after a first of the two consecutively transmitted TCC signals, opening at least one switch that connects the coupling capacitor to the transmitting electrode vector, and
closing the at least one switch at a start of the second of the two consecutively transmitted TCC signals.

15. The method of claim 13, wherein holding the coupling capacitor at the DC voltage comprises:
after a first of the two consecutively transmitted TCC signals, opening a first switch connecting the coupling capacitor to a source of the TCC signal and a second switch connecting the coupling capacitor to the transmitting electrode vector;
closing the first and second switch at a start of a second of the two consecutively transmitted TCC signals.

16. The method of claim 13, further comprising:
determining the DC voltage by detecting a voltage across the coupling capacitor; and
applying the determined DC voltage across the coupling capacitor for the time interval between the two consecutively transmitted TCC signals.

17. The method of claim 16, further comprising
determining the DC voltage with an analog-to-digital converter;
receiving the determined DC with a digital-to-analog converter; and
applying DC voltage across the coupling capacitor with the digital-to-analog converter.

18. The method of claim 17, further comprising applying the DC voltage to the coupling capacitor through a resistor coupled to the digital-to-analog converter.

19. The method of claim 13, further comprising:
receiving a cardiac electrical signal with a sensing circuit;
applying a blanking period to the sensing circuit; and
starting transmission of at least a first one of the plurality of TCC signals during the blanking period.

20. The method of claim 19, further comprising:
holding the coupling capacitor at the DC voltage for the time interval by holding the coupling capacitor at the DC voltage after a last TCC signal of a first transmission session until a first TCC signal of a second transmission session; and
starting transmission of the first TCC signal of the second transmission session outside a second blanking period applied to the sensing circuit.

21. The method of claim 13, wherein holding the coupling capacitor at the DC voltage for the time interval between two consecutively transmitted TCC signals of the plurality of TCC signals comprises holding the coupling capacitor at the DC voltage for a time interval between a last TCC signal of a first transmission session until a first TCC signal of a second transmission session.

22. The method of claim 13, further comprising
identifying by a control circuit of the IMD a physiological refractory period associated with one of an intrinsic or evoked cardiac event; and
transmission of the first one of the plurality of TCC signals during the physiological refractory period.

23. The method of claim 13, wherein holding the coupling capacitor at the DC voltage comprises holding the coupling capacitor to within five percent (5%) of the DC voltage.

24. A non-transitory, computer-readable storage medium comprising a set of instructions which, when executed by a device, cause the device to:
generate a plurality of tissue conduction communication (TCC) signals, each of the plurality of TCC signals comprising a plurality of cycles of a carrier frequency signal;
couple the generated TCC signals to a transmitting electrode vector to transmit the plurality of TCC signals via a conductive tissue pathway; and
hold the coupling capacitor at a direct current (DC) voltage for a time interval between two consecutively transmitted TCC signals of the plurality of TCC signals.

* * * * *